(12) United States Patent
Parker et al.

(10) Patent No.: US 7,364,342 B2
(45) Date of Patent: Apr. 29, 2008

(54) LIGHT REDIRECTING FILMS PATTERN OF VARIABLE OPTICAL ELEMENTS

(75) Inventors: Jeffery R. Parker, Richfield, OH (US); Timothy A. McCollum, Westlake, OH (US); Robert M. Ezell, Brunswick, OH (US)

(73) Assignee: Solid State Opto Limited (VG)

( * ) Notice: Subject to any disclaimer, the term of this patent is extended or adjusted under 35 U.S.C. 154(b) by 0 days.

(21) Appl. No.: 11/484,063

(22) Filed: Jul. 11, 2006

(65) Prior Publication Data

US 2006/0256577 A1 Nov. 16, 2006

Related U.S. Application Data

(60) Division of application No. 10/729,113, filed on Dec. 5, 2003, now Pat. No. 7,090,389, which is a division of application No. 09/909,318, filed on Jul. 19, 2001, now Pat. No. 6,752,505, which is a continuation-in-part of application No. 09/256,275, filed on Feb. 23, 1999, now Pat. No. 6,712,481.

(51) Int. Cl.
G02B 6/10 (2006.01)
F21V 7/04 (2006.01)

(52) U.S. Cl. ............... 362/626; 362/606; 362/608; 362/620; 362/627; 385/131

(58) Field of Classification Search ......... 362/615, 362/618, 619, 620, 624, 625, 626, 606, 608, 362/627; 385/131; 349/65, 69, 70
See application file for complete search history.

(56) References Cited

U.S. PATENT DOCUMENTS

| | | | |
|---|---|---|---|
| 3,043,947 A * | 7/1962 | Albinger, Jr. | ............... 362/634 |
| 4,373,282 A | 2/1983 | Wragg | |
| 4,460,940 A | 7/1984 | Mori | |
| 4,542,449 A | 9/1985 | Whitehead | |
| 4,729,068 A * | 3/1988 | Ohe | ............... 362/615 |
| 4,906,070 A | 3/1990 | Cobb, Jr. | |
| 5,056,892 A | 10/1991 | Cobb, Jr. | |
| 5,375,043 A | 12/1994 | Tokunaga | |
| 5,377,084 A | 12/1994 | Kojima et al. | |
| 5,386,347 A * | 1/1995 | Matsumoto | ............... 362/623 |
| 5,390,436 A * | 2/1995 | Ashall | ............... 40/546 |
| 5,396,350 A | 3/1995 | Beeson et al. | |
| 5,477,422 A * | 12/1995 | Hooker et al. | ............... 362/29 |
| 5,550,676 A * | 8/1996 | Ohe et al. | ............... 359/599 |
| 5,598,281 A | 1/1997 | Zimmerman et al. | |
| 5,600,462 A | 2/1997 | Suzuki et al. | |
| 5,618,096 A * | 4/1997 | Parker et al. | ............... 362/629 |

(Continued)

FOREIGN PATENT DOCUMENTS

WO WO 96/27757 9/1996

(Continued)

*Primary Examiner*—Ismael Negron
(74) *Attorney, Agent, or Firm*—Renner, Otto, Boisselle & Sklar, LLP

(57) ABSTRACT

Light redirecting films and film systems include a thin optically transparent substrate having a pattern of individual optical elements of well defined shape on or in the substrate. At least some of the optical elements may vary at different locations on the substrate to redistribute or redirect light passing through the substrate.

42 Claims, 18 Drawing Sheets

U.S. PATENT DOCUMENTS

| | | |
|---|---|---|
| 5,641,219 A | 6/1997 | Mizobe |
| 5,649,754 A * | 7/1997 | Matsumoto ................. 362/618 |
| 5,695,269 A | 12/1997 | Lippmann et al. |
| 5,719,649 A | 2/1998 | Shono et al. |
| 5,771,328 A | 6/1998 | Wortman et al. |
| 5,775,791 A | 7/1998 | Yoshikawa et al. |
| 5,779,338 A | 7/1998 | Ishikawa et al. |
| 5,844,720 A | 12/1998 | Ohara et al. |
| 5,890,791 A | 4/1999 | Saito |
| 5,917,664 A | 6/1999 | O'Neill et al. |
| 5,919,551 A | 7/1999 | Cobb, Jr. et al. |
| 5,921,651 A * | 7/1999 | Ishikawa ..................... 362/624 |
| 5,931,555 A * | 8/1999 | Akahane et al. ............. 362/613 |
| 5,944,405 A * | 8/1999 | Takeuchi et al. ............ 362/617 |
| 5,961,198 A | 10/1999 | Hira et al. |
| 6,027,221 A | 2/2000 | Ishikawa et al. |
| 6,091,547 A | 7/2000 | Gardiner et al. |
| 6,120,280 A | 9/2000 | Mimura et al. |
| 6,151,169 A | 11/2000 | Kim |
| 6,712,481 B2 * | 3/2004 | Parker et al. ............... 362/619 |
| 6,752,505 B2 * | 6/2004 | Parker et al. ............... 362/627 |
| 7,090,389 B2 * | 8/2006 | Parker et al. ............... 362/627 |

FOREIGN PATENT DOCUMENTS

| | | |
|---|---|---|
| WO | WO 98/50806 | 11/1998 |
| WO | WO 99/42861 | 8/1999 |
| WO | WO 01/27527 | 4/2001 |
| WO | WO 01/27663 | 4/2001 |

* cited by examiner

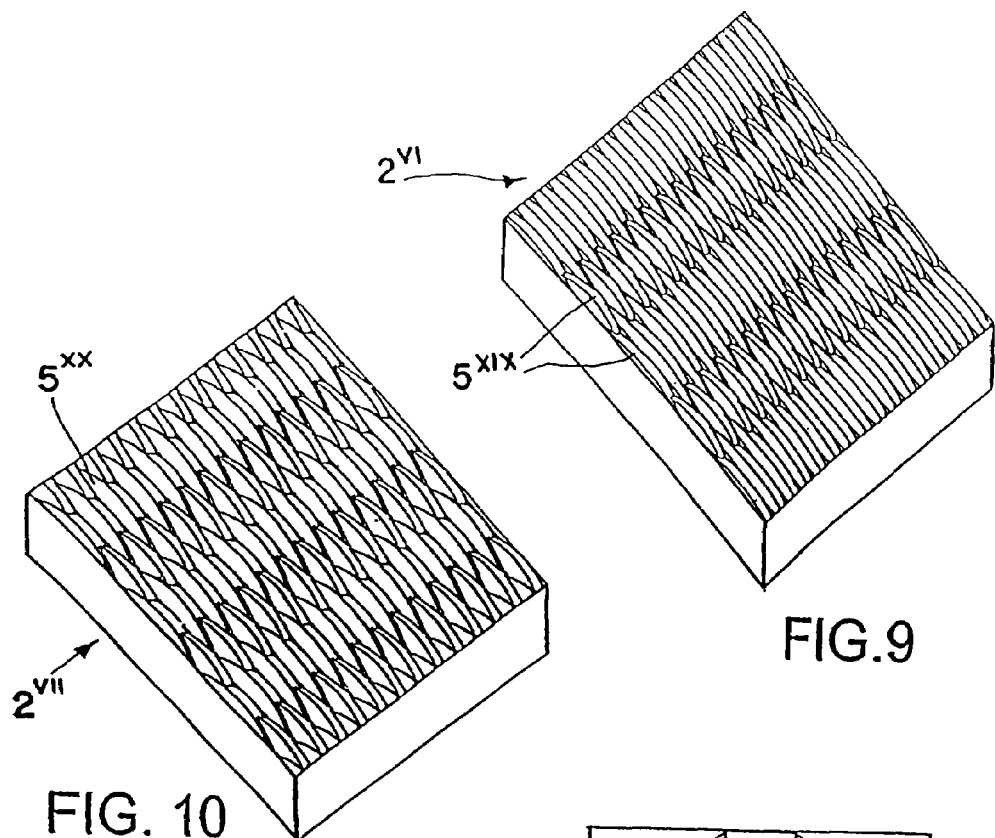
FIG. 9
FIG. 10
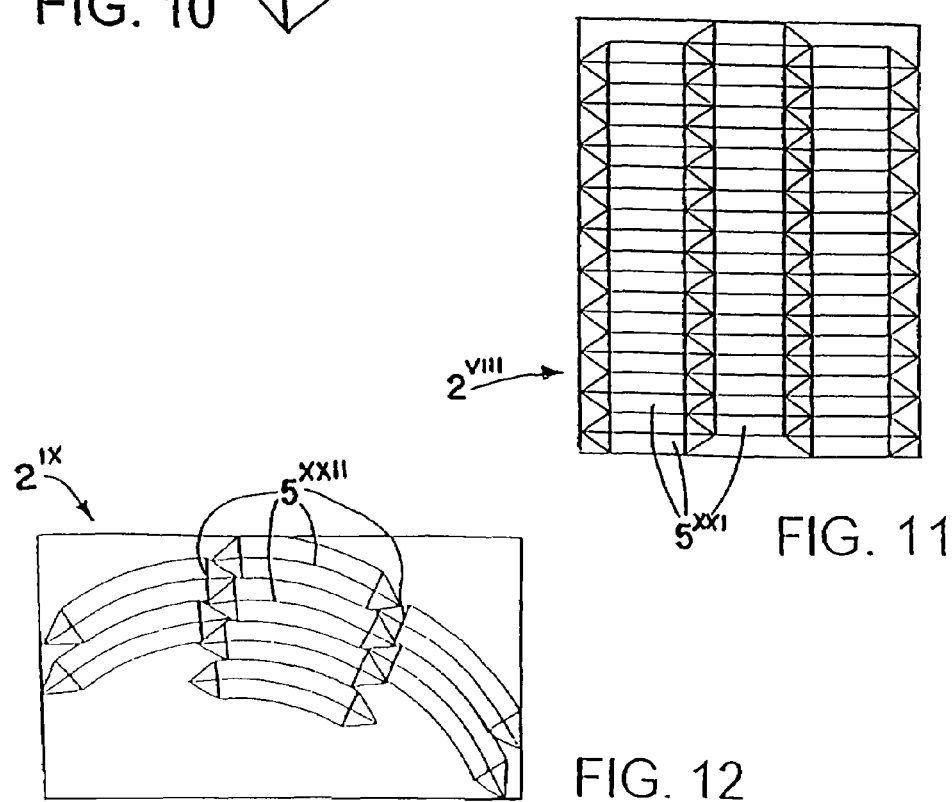
FIG. 11
FIG. 12

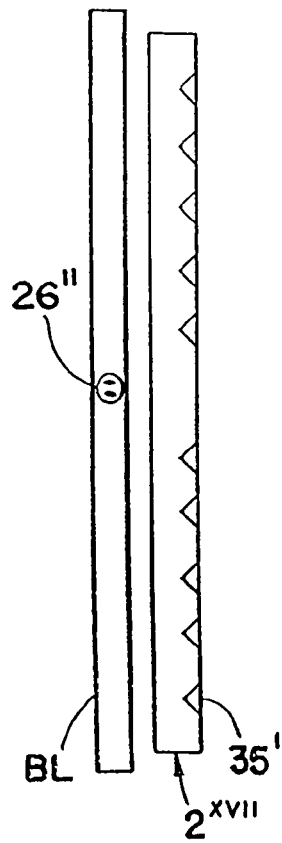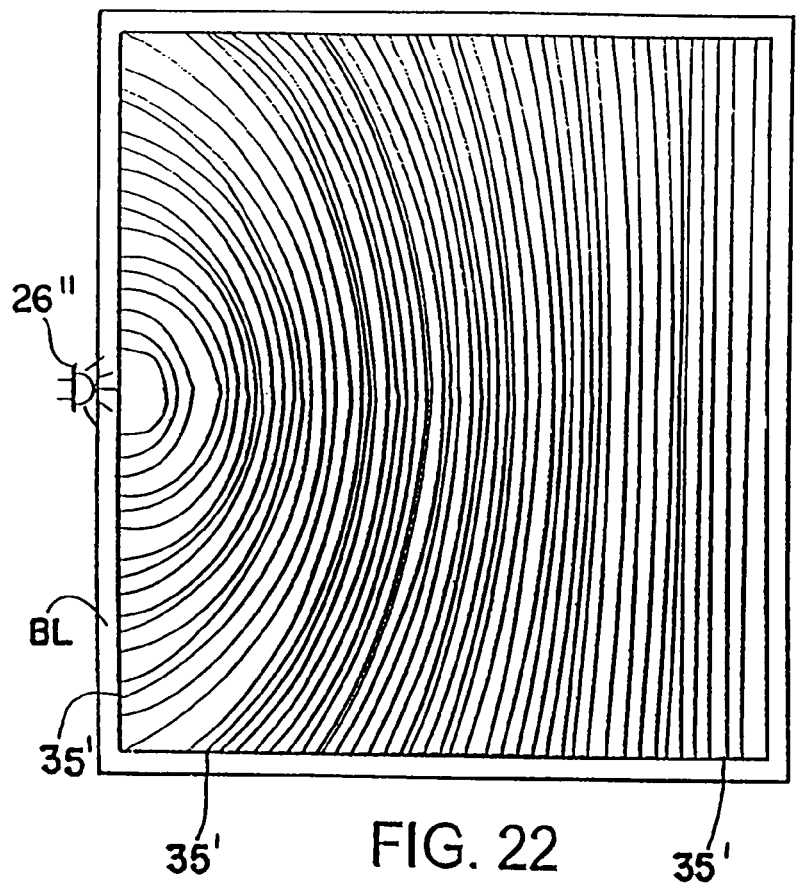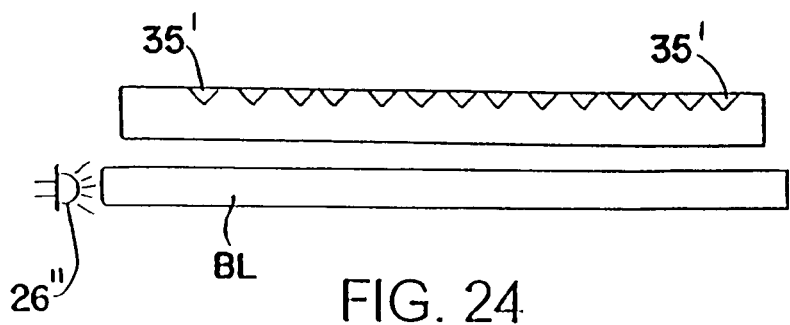
FIG. 23
FIG. 22
FIG. 24

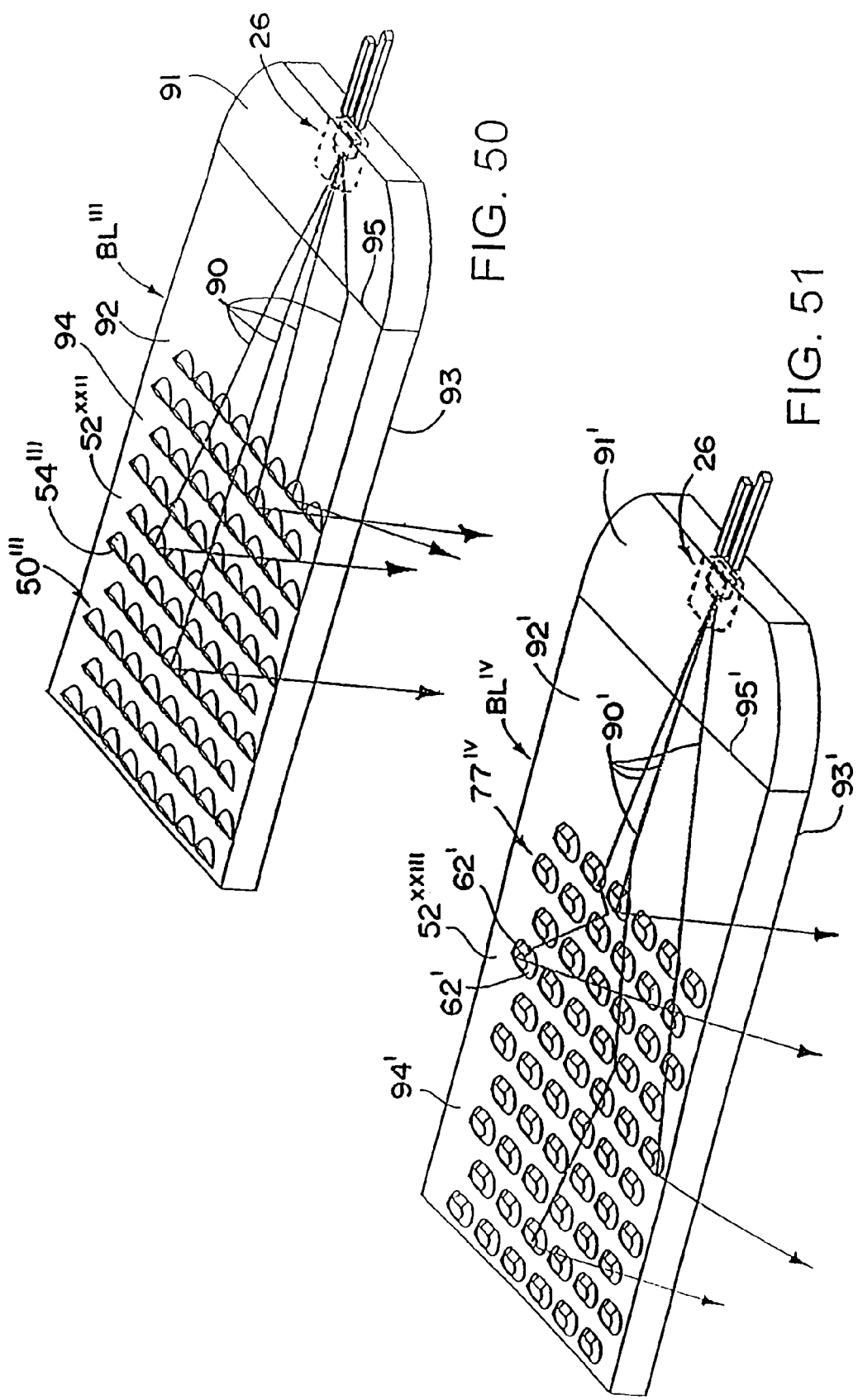

LIGHT REDIRECTING FILMS PATTERN OF VARIABLE OPTICAL ELEMENTS

CROSS-REFERENCE TO RELATED APPLICATIONS

This application is a division of U.S. patent application Ser. No. 10/729,113, filed Dec. 5, 2003 now U.S. Pat. No. 7,090,389, which is a division of U.S. patent application Ser. No. 09/909,318, filed Jul. 19, 2001, now U.S. Pat. No. 6,752,505, which is a continuation-in-part of U.S. patent application Ser. No. 09/256,275, filed Feb. 23, 1999, now U.S. Pat. No. 6,712,481, the entire disclosures of which are incorporated herein by reference.

FIELD OF THE INVENTION

This invention relates to light redirecting films and film systems for redirecting light from a light source toward a direction normal to the plane of the films.

BACKGROUND OF THE INVENTION

Light redirecting films are thin transparent or translucent optical films or substrates that redistribute the light passing through the films such that the distribution of the light exiting the films is directed more normal to the surface of the films. Heretofore, light redirecting films were provided with prismatic grooves, lenticular grooves, or pyramids on the light exit surface of the films which changed the angle of the film/air interface for light rays exiting the films and caused the components of the incident light distribution traveling in a plane perpendicular to the refracting surfaces of the grooves to be redistributed in a direction more normal to the surface of the films. Such light redirecting films are used, for example, with liquid crystal displays, used in laptop computers, word processors, avionic displays, cell phones, PDAs and the like to make the displays brighter.

The light entrance surface of the films usually has a transparent or matte finish depending on the visual appearance desired. A matte finish produces a softer image but is not as bright due to the additional scattering and resultant light loss caused by the matte or diffuse surface.

Heretofore, most applications used two grooved film layers rotated relative to each other such that the grooves in the respective film layers are at 90 degrees relative to each other. The reason for this is that a grooved light redirecting film will only redistribute, towards the direction normal to the film surface, the components of the incident light distribution traveling in a plane perpendicular to the refracting surfaces of the grooves. Therefore, to redirect light toward the normal of the film surface in two dimensions, two grooved film layers rotated 90 degrees with respect to each other are needed, one film layer to redirect light traveling in a plane perpendicular to the direction of its grooves and the other film layer to redirect light traveling in a plane perpendicular to the direction of its grooves.

Attempts have been made in the past to create a single layer light redirecting film that will redirect components of the incident light distribution traveling along two different axes 90 degrees to each other. One known way of accomplishing this is to provide a single layer film with two sets of grooves extending perpendicular to each other resulting in a pyramid structure which redirects light traveling in both such directions. However, such a film produces a much lower brightness than two film layers each with a single groove configuration rotated 90 degrees with respect to each other because the area that is removed from the first set of grooves by the second set of grooves in a single layer film reduces the surface area available to redirect light substantially by 50% in each direction of travel.

In addition, heretofore, the grooves of light redirecting films have been constructed so that all of the grooves meet the surface of the films at the same angle, mostly 45 degrees. This design assumes a constant, diffuse angular distribution of light from the light source, such as a lambertian source, a backlighting panel using a printing or etching technology to extract light, or a backlighting panel behind heavy diffusers. A light redirecting film where all of the light redirecting surfaces meet the film at the same angle is not optimized for a light source that has a nonuniform directional component to its light emission at different areas above the source. For example, the average angle about which a modern high efficiency edge lit backlight, using grooves or micro-optical surfaces to extract light, changes at different distances from the light source, requiring a different angle between the light redirecting surfaces and the plane of the film to optimally redirect light toward the normal of the film.

There is thus a need for a light redirecting film that can produce a softer image while eliminating the decrease in brightness associated with a matte or diffuse finish on the light input side of the film. Also, there is a need for a single layer of film which can redirect a portion of the light traveling in a plane parallel to the refracting surfaces in a grooved film, that would be brighter than a single layer of film using prismatic or lenticular grooves. In addition, there is a need for a light redirecting film that can compensate for the different angular distributions of light that may exist for a particular light source at different positions above the source, such as backlights used to illuminate liquid crystal displays. Also, there is a need for a light redirecting film system in which the film is matched or tuned to the light output distribution of a backlight or other light source to reorient or redirect more of the incident light from the backlight within a desired viewing angle.

SUMMARY OF THE INVENTION

The present invention relates to light redirecting films and light redirecting film systems that redistribute more of the light emitted by a backlight or other light source toward a direction more normal to the plane of the films, and to light redirecting films that produce a softer image without the brightness decrease associated with films that have a matte or diffuse finish on the light entrance surface of the films, for increased effectiveness.

The light exit surface of the films has a pattern of discrete individual optical elements of well defined shape for refracting the incident light distribution such that the distribution of light exiting the films is in a direction more normal to the surface of the films. These individual optical elements may be formed by depressions in or projections on the exit surface of the films, and include one or more sloping surfaces for refracting the incident light toward a direction normal to the exit surface. These sloping surfaces may for example include a combination of planar and curved surfaces that redirect the light within a desired viewing angle. Also, the curvature of the surfaces, or the ratio of the curved area to the planar area of the individual optical elements as well as the perimeter shapes of the curved and planar surfaces may be varied to tailor the light output distribution of the films, to customize the viewing angle of the display device used in conjunction with the films. In addition, the curvature of the surfaces, or the ratio of the curved area to the planar area of the individual optical elements may be varied to redirect more or less light that is traveling in a plane that would be parallel to the grooves of a prismatic or lenticular grooved film. Also the size and population of the individual optical elements, as well as the curvature of the surfaces of the individual optical elements may be chosen to produce a more or less diffuse output or to randomize the input light distribution from the light source to produce a softer more diffuse light output distribution while maintaining the output distribution within a specified angular region about the direction normal to the films.

The light entrance surface of the films may have an optical coating such as an antireflective coating, a reflective polarizer, a retardation coating or a polarizer. Also a matte or diffuse texture may be provided on the light entrance surface depending on the visual appearance desired. A matte finish produces a softer image but is not as bright.

The individual optical elements on the exit surface of the films may be randomized in such a way as to eliminate any interference with the pixel spacing of a liquid crystal display. This randomization can include the size, shape, position, depth, orientation, angle or density of the optical elements. This eliminates the need for diffuser layers to defeat moiré and similar effects. Also, at least some of the individual optical elements may be arranged in groupings across the exit surface of the films, with at least some of the optical elements in each of the groupings having a different size or shape characteristic that collectively produce an average size or shape characteristic for each of the groupings that varies across the films to obtain average characteristic values beyond machining tolerances for any single optical element and to defeat moiré and interference effects with the pixel spacing of a liquid crystal display. In addition, at least some of the individual optical elements may be oriented at different angles relative to each other for customizing the ability of the films to reorient/redirect light along two different axes.

The angles that the light redirecting surfaces of the individual optical elements make with the light exit surface of the films may also be varied across the display area of a liquid crystal display to tailor the light redirecting function of the films to a light input distribution that is non-uniform across the surface of the light source.

The individual optical elements of the light redirecting films also desirably overlap each other, in a staggered, interlocked and/or intersecting configuration, creating an optical structure with excellent surface area coverage. Moreover, the individual optical elements may be arranged in groupings with some of the individual optical elements oriented along one axis and other individual optical elements oriented along another axis. Also, the orientation of the individual optical elements in each grouping may vary. Further, the size, shape, position and/or orientation of the individual optical elements of the light redirecting films may vary to account for variations in the distribution of light emitted by a light source.

The properties and pattern of the optical elements of light redirecting films may also be customized to optimize the light redirecting films for different types of light sources which emit different light distributions, for example, one pattern for single bulb laptops, another pattern for double bulb flat panel displays, and so on.

Further, light redirecting film systems are provided in which the orientation, size, position and/or shape of the individual optical elements of the light redirecting films are tailored to the light output distribution of a backlight or other light source to reorient or redirect more of the incident light from the backlight within a desired viewing angle. Also, the backlight may include individual optical deformities that collimate light along one axis and the light redirecting films may include individual optical elements that collimate light along another axis perpendicular to the one axis.

To the accomplishment of the foregoing and related ends, the invention, then, comprises the features hereinafter more fully described and particularly pointed out in the claims, the following description and annexed drawings setting forth in detail certain illustrative embodiments of the invention, these being indicative, however, of but several of the various ways in which the principles of the invention may be employed.

BRIEF DESCRIPTION OF THE DRAWINGS

In the annexed drawings:

FIGS. 5-20 are schematic perspective or plan views showing different patterns of individual optical elements on light redirecting films of the present invention;

FIG. 22 is a top plan view of a light redirecting film having a pattern of optical grooves extending across the film facing a midpoint on one edge of the film that decreases in curvature as the distance from the one edge increases;

FIG. 23 is an end elevation view of the light redirecting film of FIG. 22 as seen from the left end thereof;

FIG. 24 is a side elevation view of the light redirecting film of FIG. 22;

FIGS. 50 and 51 are enlarged perspective views schematically showing how exemplary light rays emitted from a focused light source are reflected or refracted by different individual optical deformities of well defined shapes of a backlight surface area.

DETAILED DESCRIPTION OF THE INVENTION

Figure 1:
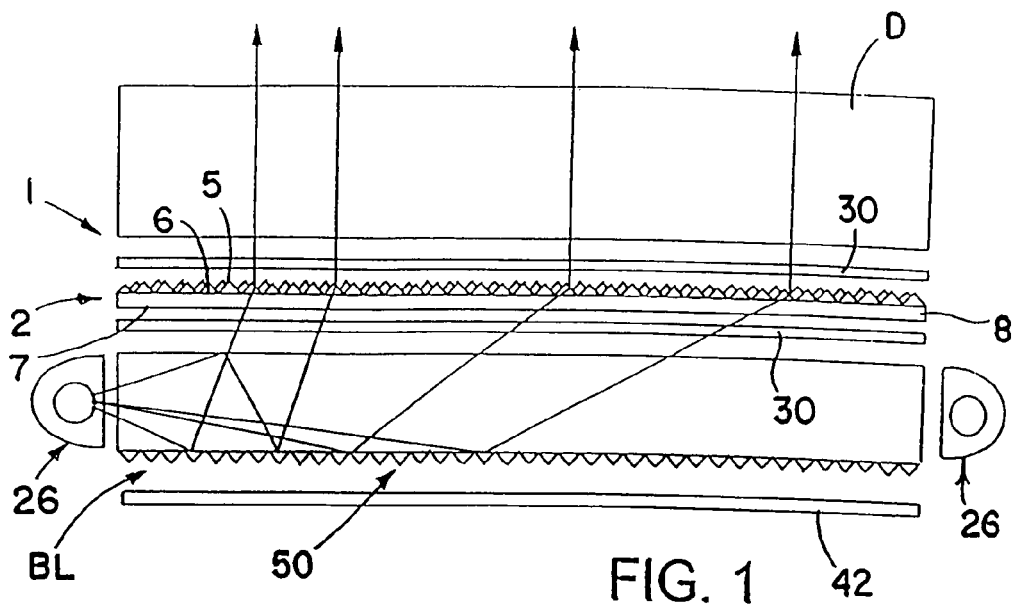
FIG. 1 is a schematic side elevation view of one form of light redirecting film system in accordance with the present invention.
Figure 2:
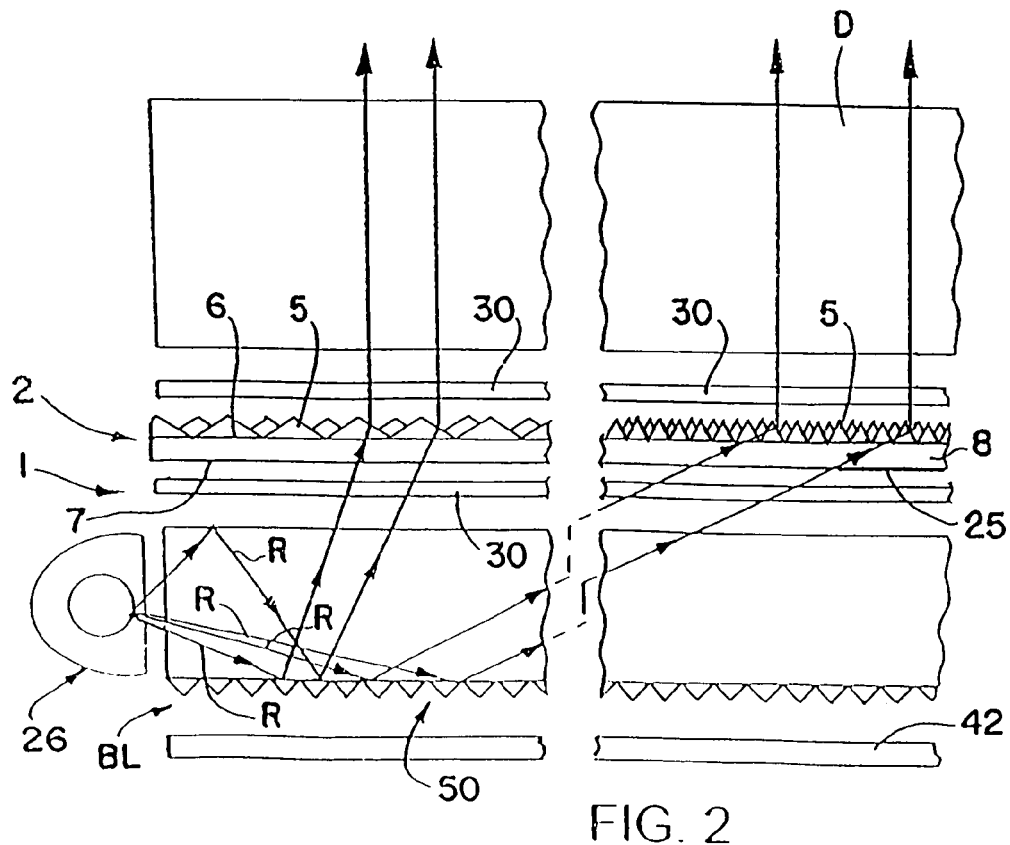
FIG. 2 is an enlarged fragmentary side elevation view of a portion of the backlight and light redirecting film system of FIG. 1.

FIGS. 1 and 2 schematically show one form of light redirecting film system 1 in accordance with this invention including a light redirecting film 2 that redistributes more of the light emitted by a backlight BL or other light source toward a direction more normal to the surface of the film. Film 2 may be used to redistribute light within a desired viewing angle from almost any light source for lighting, for example, a display such as a liquid crystal display, used in laptop computers, word processors, avionic displays, cell phones, PDAs and the like, to make the displays brighter. The liquid crystal display can be any type including a transmissive liquid crystal display D as schematically shown in FIGS. 1 and 2, a reflective liquid crystal display $D^I$ as schematically shown in FIG. 3 and a transflective liquid crystal display $D^{II}$ as schematically shown in FIG. 4.

Figure 3:
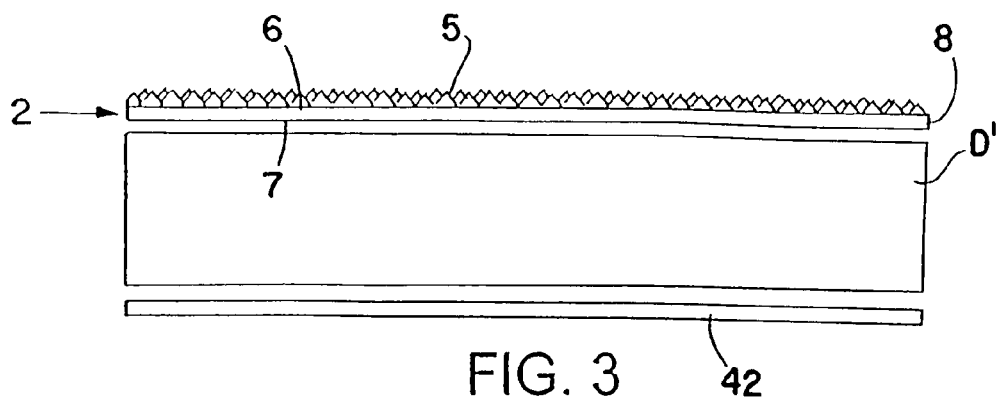
FIGS. 3 and 4 are schematic side elevation views of other forms of light redirecting film systems of the present invention.

The reflective liquid crystal display $D^I$ shown in FIG. 3 includes a back reflector 42 adjacent the back side for reflecting ambient light entering the display back out the display to increase the brightness of the display. The light redirecting film 2 of the present invention is placed adjacent the top of the reflective liquid crystal display to redirect ambient light (or light from a front light) into the display toward a direction more normal to the plane of the film for reflection back out by the back reflector within a desired viewing angle to increase the brightness of the display. Light redirecting film 2 may be attached to, laminated to or otherwise held in place against the top of the liquid crystal display.

Figure 4:
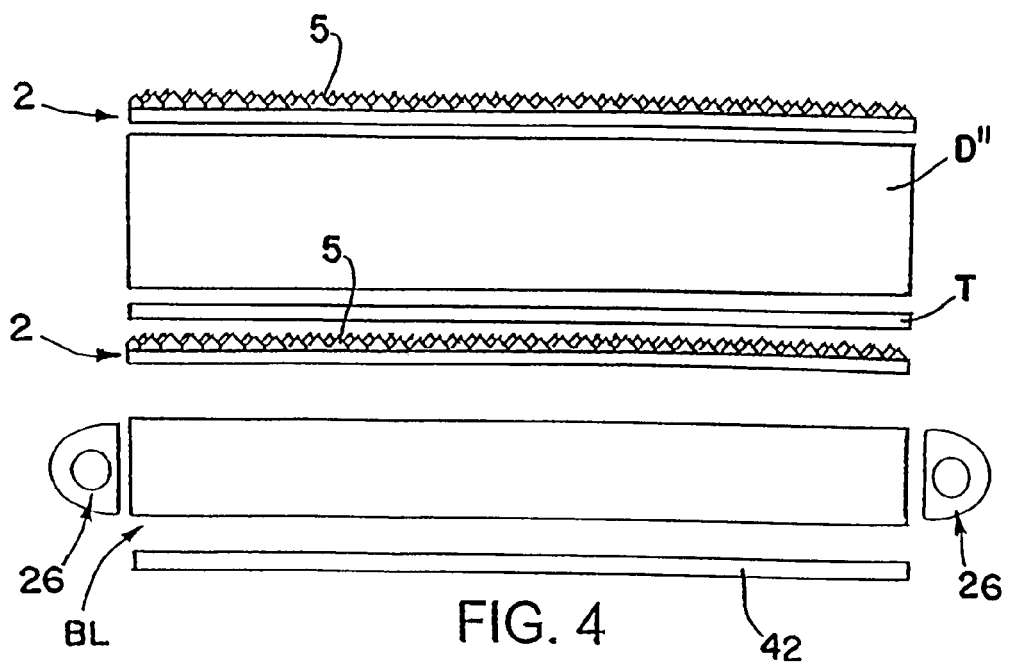

The transflective liquid crystal display $D^{II}$ shown in FIG. 4 includes a transreflector T placed between the display and a backlight BL for reflecting ambient light entering the front of the display back out the display to increase the brightness of the display in a lighted environment, and for transmitting light from the backlight through the transreflector and out the display to illuminate the display in a dark environment. In this embodiment the light redirecting film 2 may either be placed adjacent the top of the display or adjacent the bottom of the display or both as schematically shown in FIG. 4 for redirecting or redistributing ambient light and/or light from the backlight more normal to the plane of the film to make the light ray output distribution more acceptable to travel through the display to increase the brightness of the display.

Light redirecting film 2 comprises a thin transparent film or substrate 8 having a pattern of discrete individual optical elements 5 of well defined shape on the light exit surface 6 of the film for refracting the incident light distribution such that the distribution of the light exiting the film is in a direction more normal to the surface of the film.

Figure 5:
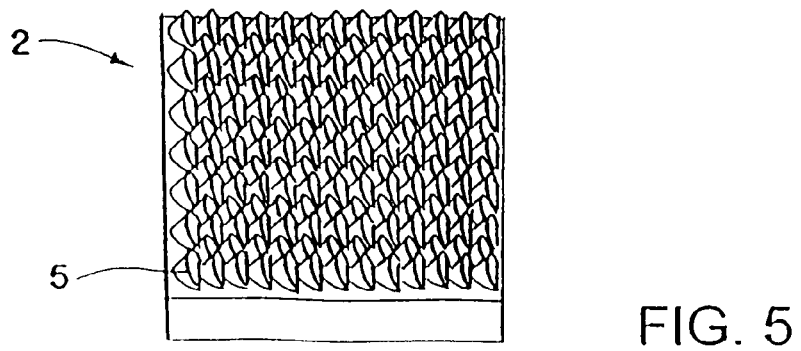
Figure 5A:
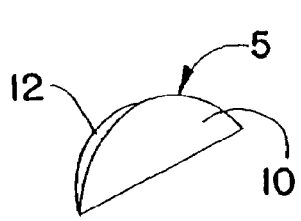
FIGS. 5a-5n are schematic perspective views of different geometric shapes that the individual optical elements on the light redirecting films may take.
Figure 5B:
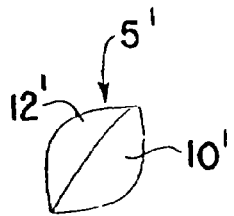

Each of the individual optical elements 5 has a width and length many times smaller than the width and length of the film, and may be formed by depressions in or projections on the exit surface of the film. These individual optical elements 5 include at least one sloping surface for refracting the incident light toward the direction normal to the light exit surface. FIG. 5 shows one pattern of individual optical elements 5 on a film 2. These optical elements may take many different shapes. For example, FIG. 5a shows one of the optical elements 5 of FIG. 5 which is a non-prismatic optical element having a total of two surfaces 10, 12, both of which are sloping. One of the surfaces 10 shown in FIG. 5a is planar or flat whereas the other surface 12 is curved. Moreover, both surfaces 10, 12 intersect each other and also intersect the surface of the film. Alternatively, both surfaces $10^I$, $12^I$ of the individual optical elements $5^I$ may be curved as schematically shown in FIG. 5b.

Figure 5C:
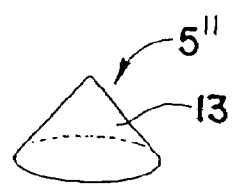
Figure 5D:
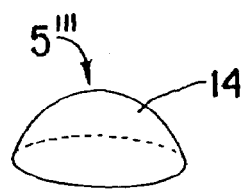

Alternatively, the optical elements may each have only one surface that is curved and sloping and intersects the film. FIG. 5c shows one such optical element $5^{II}$ in the shape of a cone 13, whereas FIG. 5d shows another such optical element $5^{III}$ having a semispherical or dome shape 14. Also, such optical elements may have more than one sloping surface intersecting the film.

Figure 5E:
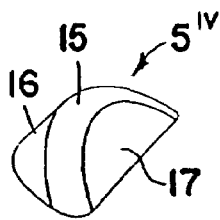

FIG. 5e shows an optical element $5^{IV}$ having a total of three surfaces, all of which intersect the film and intersect each other. Two of the surfaces 15 and 16 are curved, whereas the third surface 17 is planar.

Figure 5F:
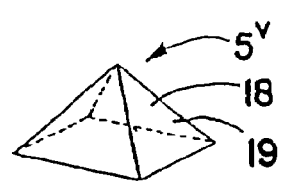
Figure 5G:
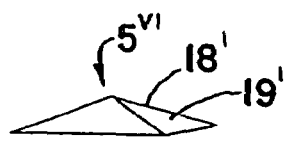
Figure 5H:
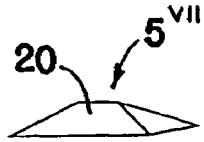
Figure 5I:
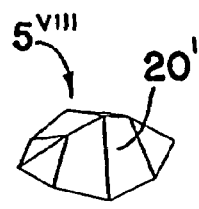

FIG. 5f shows an optical element $5^V$ in the shape of a pyramid 18 with four triangular shaped sides 19 that intersect each other and intersect the film. The sides 19 of the pyramid 18 may all be of the same size and shape as shown in FIG. 5f, or the sides $19^I$ of the pyramid $18^I$ may be stretched so the sides of the optical element $5^{VI}$ have different perimeter shapes as shown in FIG. 5g. Also, the optical elements may have any number of planar sloping sides. FIG. 5h shows an optical element $5^{VII}$ with four planar sloping sides 20, whereas FIG. 5i shows an optical element $5^{VIII}$ with eight planar sloping sides $20^I$.

Figure 5J:
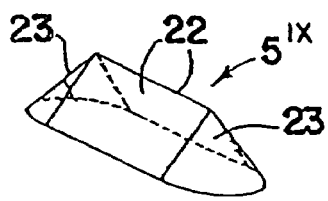
Figure 5K:
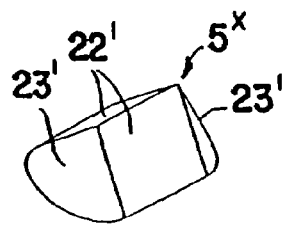
Figure 5L:
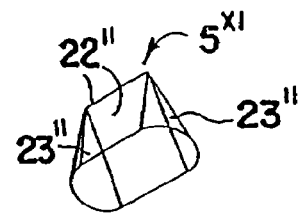
Figure 5M:
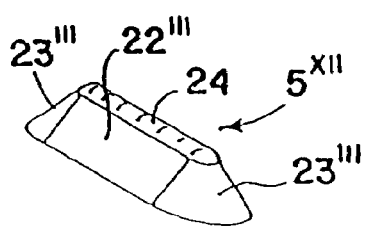
Figure 5N:
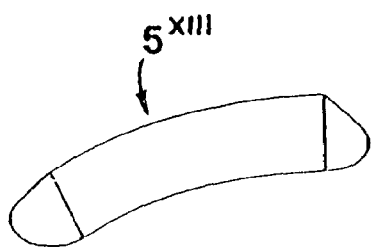
Figure 6:
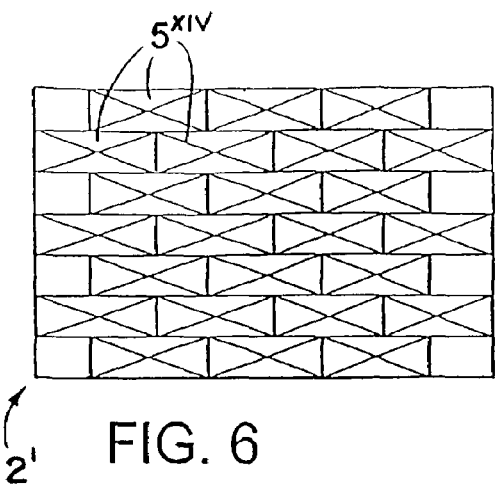

The individual optical elements 5 may also have more than one curved and more than one planar sloping surface, all intersecting the film. FIG. 5j shows an optical element $5^{IX}$ having a pair of intersecting oppositely sloping planar sides 22 and oppositely rounded or curved ends or sides 23. Further, the sloping planar sides $22^I$ and $22^{II}$ and curved ends or sides $23^I$ and $23^{II}$ of optical elements $5^X$ and $5^{XI}$ may have different angled slopes as shown in FIGS. 5k and 5l. Moreover, the optical elements may have at least one curved surface that does not intersect the film. One such optical element $5^{XII}$ is shown in FIG. 5m which includes a pair of oppositely sloping planar sides $22^{III}$ and oppositely rounded or curved ends or sides $23^{III}$ and a rounded or curved top 24 intersecting the oppositely sloping sides and oppositely rounded ends. Further, the optical elements $5^{XIII}$ may be curved along their length as shown in FIG. 5n.

Providing the individual optical elements 5 with a combination of planar and curved surfaces redirects or redistributes a larger viewing area than is possible with a grooved film. Also, the curvature of the surfaces, or the ratio of the curved area to the planar area of the individual optical elements may be varied to tailor the light output distribution of the film to customize the viewing area of a display device used in conjunction with the film.

The light entrance surface 7 of the film 2 may have an optical coating 25 (see FIG. 2) such as an antireflective coating, a reflective polarizer, a retardation coating or a polarizer. Also, a matte or diffuse texture may be provided on the light entrance surface 7 depending on the visual appearance desired. A matte finish produces a softer image but is not as bright. The combination of planar and curved surfaces of the individual optical elements of the present invention may be configured to redirect some of the light rays impinging thereon in different directions to produce a softer image without the need for an additional diffuser or matte finish on the entrance surface of the film.

Figure 7:
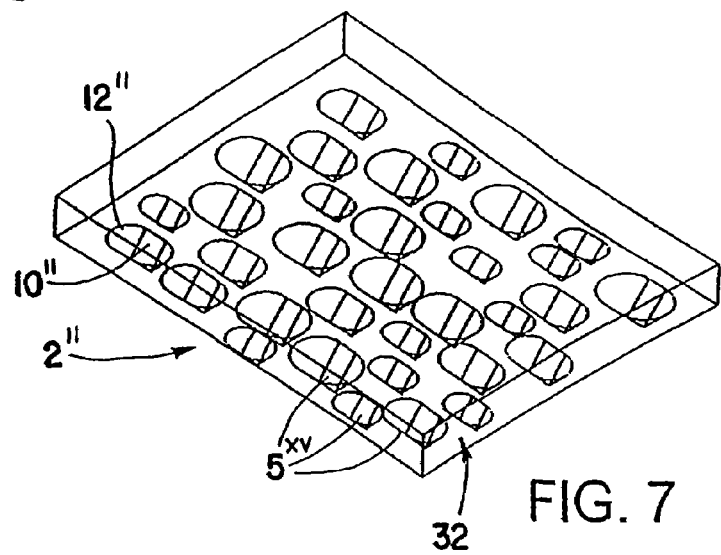
Figure 8:
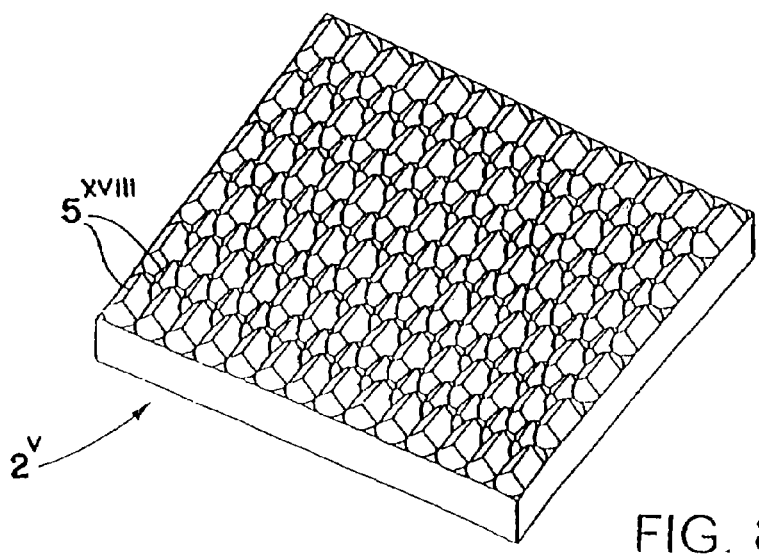

The individual optical elements of the light redirecting film also desirably overlap each other in a staggered, interlocked and/or intersecting configuration, creating an optical structure with excellent surface area coverage. FIGS. 6, 7, 13 and 15, for example, show optical elements $5^{XIV}$, $5^{XV}$, $5^{XVI}$, and $5^{XVII}$ of light redirecting films $2^I$, $2^{II}$, $2^{III}$ and $2^{IV}$ staggered with respect to each other; FIGS. 8-10 show the optical elements $5^{XVIII}$, $5^{XIX}$ and $5^{XX}$ of light redirecting films $2^V$, $2^{VI}$ and $2^{VII}$ intersecting each other; and FIGS. 11 and 12 show the optical elements $5^{XXI}$ and $5^{XXII}$ of light redirecting films $2^{VIII}$ and $2^{IX}$ interlocking each other.

Moreover, the slope angle, density, position, orientation, height or depth, shape, and/or size of the optical elements of the light redirecting film may be matched or tuned to the particular light output distribution of a backlight BL or other light source to account for variations in the distribution of light emitted by the backlight in order to redistribute more of the light emitted by the backlight within a desired viewing angle. For example, the angle that the sloping surfaces (e.g., surfaces 10, 12) of the optical elements 5 make with the surface of the light redirecting film 2 may be varied as the distance from the backlight BL from a light source 26 increases to account for the way the backlight emits light rays R at different angles as the distance from the light source increases as schematically shown in FIG. 2. Also, the backlight BL itself may be designed to emit more of the light rays at lower angles to increase the amount of light emitted by the backlight and rely on the light redirecting film to redistribute more of the emitted light within a desired viewing angle. In this way the individual optical elements of the light redirecting film may be selected to work in conjunction with the optical deformations of the backlight to produce an optimized output light ray angle distribution from the system.

Figure 13:
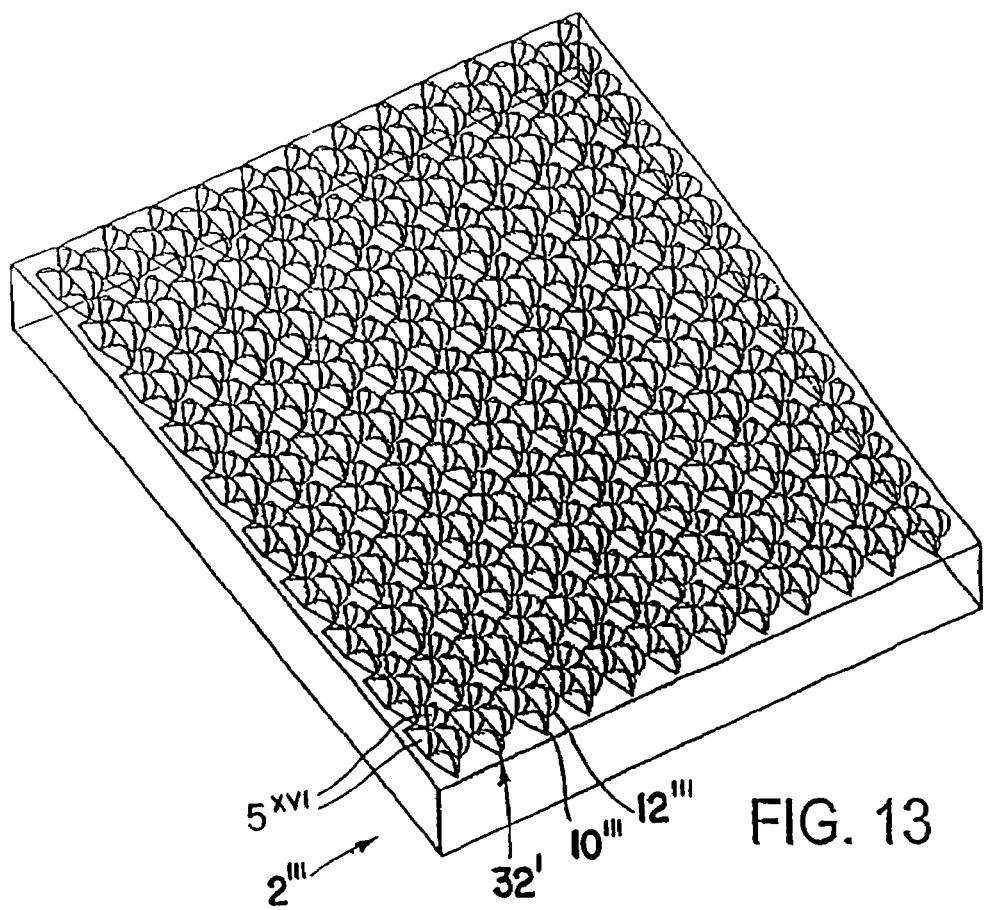
Figure 14:
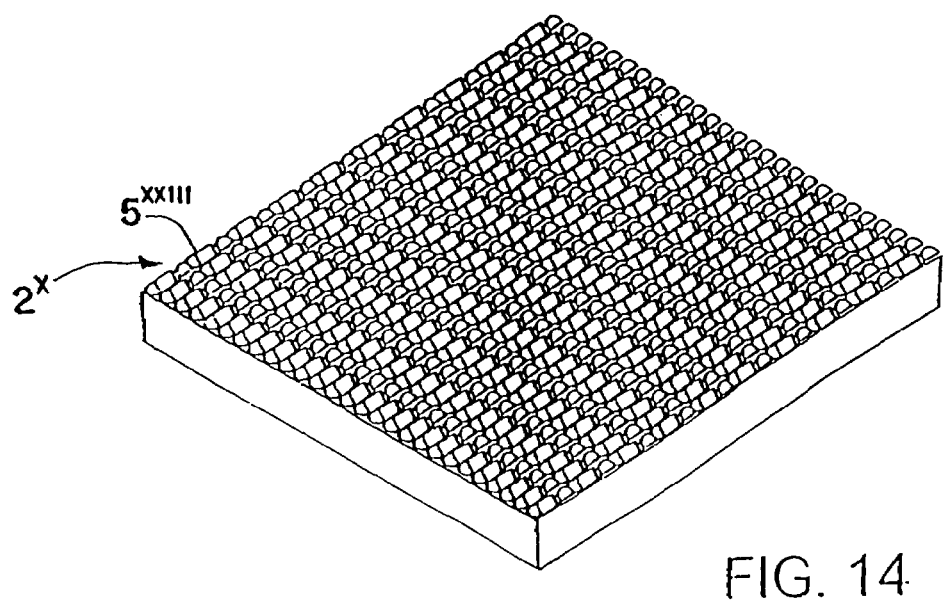

FIGS. 2, 5 and 9 show different patterns of individual optical elements all of the same height or depth, whereas FIGS. 7, 8, 10, 13 and 14 show different patterns of individual optical elements of different shapes, sizes and height or depth. The individual optical elements $5^{XXIII}$ of the light redirecting film $2^X$ of FIG. 14 are also shown arranged in alternating rows along the width or length of the film.

Figure 15:
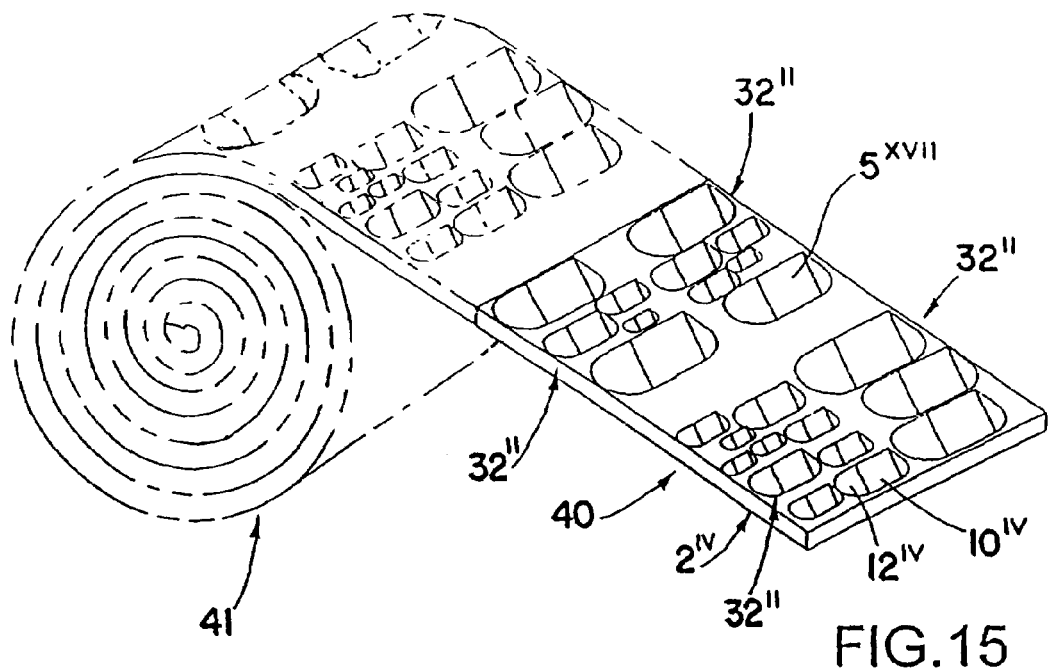
Figure 16:
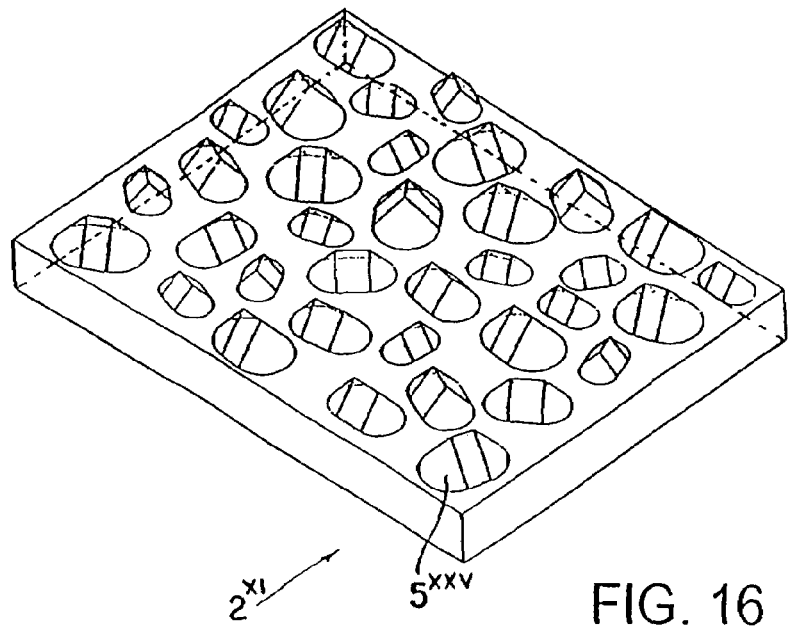
Figure 17:
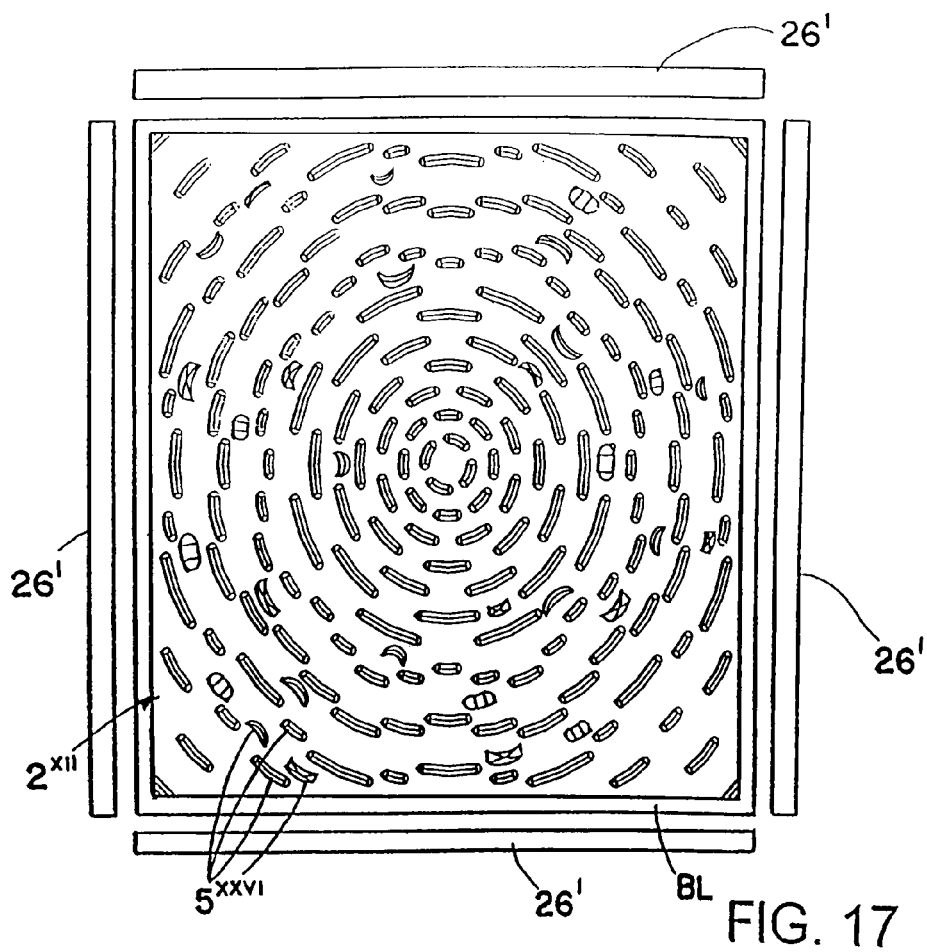

The individual optical elements $5^{XXV}$ and $5^{XXVI}$ may also be randomized on the film $2^{XI}$ and $2^{XII}$ as schematically shown in FIGS. 16 and 17 in such a way as to eliminate any interference with the pixel spacing of a liquid crystal display. This eliminates the need for optical diffuser layers 30 shown in FIGS. 1 and 2 to defeat moiré and similar effects. Moreover, at least some of the individual optical elements may be arranged in groupings 32, $32^I$ and $32^{II}$ across the film, with at least some of the optical elements 5 in each grouping having a different size or shape characteristic that collectively produce an average size or shape characteristic for each of the groupings that varies across the film as schematically shown in FIGS. 7, 13 and 15 to obtain characteristic values beyond machining tolerances to defeat moiré and interference effects with the liquid crystal display pixel spacing. For example, at least some of the optical elements in each grouping may have a different depth or height that collectively produce an average depth or height characteristic for each grouping that varies across the film. Also, at least some of the optical elements in each grouping may have a different slope angle that collectively produce an average slope angle for each grouping that varies across the film. Further, at least one sloping surface of the individual optical elements in each grouping may have a different width or length that collectively produce an average width or length characteristic in each grouping that varies across the film.

Where the individual optical elements include a combination of planar and curved surfaces, for example planar and curved surfaces $10^{II}$, $12^{II}$, $10^{III}$, $12^{III}$ and $10^{IV}$, $12^{IV}$ as shown in FIGS. 7, 13 and 15, respectively, the curvature of the curved surfaces, or the ratio of the curved area to the planar area of the individual optical elements as well as the perimeter shapes of the curved and planar surfaces may be varied to tailor the light output distribution of the film. In addition, the curvature of the curved surfaces, or the ratio of the curved area to the planar area of the individual optical elements may be varied to redirect more or less light that is traveling in a plane that would be parallel to the grooves of a prismatic or lenticular grooved film, partially or completely replacing the need for a second layer of light redirecting film. Also, at least some of the individual optical elements may be oriented at different angles relative to each other as schematically shown in FIGS. 13 and 16 to redistribute more of the light emitted by a light source along two different axes in a direction more normal to the surface of the film, partially or completely replacing the need for a second layer of light redirecting film. However, it will be appreciated that two layers of such light redirecting film each having the same or different patterns of individual optical elements thereon may be placed between a light source and viewing area with the layers rotated 90 degrees (or other angles greater than 0 degrees and less than 90 degrees) with respect to each other so that the individual optical elements on the respective film layers redistribute more of the light emitted by a light source traveling in different planar directions in a direction more normal to the surface of the respective films.

Also, the light redirecting film $2^{IV}$ may have a pattern of optical elements $5^{XVII}$ that varies at different locations on the film as schematically shown in FIG. 15 to redistribute the light ray output distribution from different locations of a backlight or other light source to redistribute the light ray output distribution from the different locations toward a direction normal to the film.

Further, the properties and pattern of the optical elements of the light redirecting film may be customized to optimize the light redirecting film for different types of light sources which emit different light distributions, for example, one pattern for single bulb laptops, another pattern for double bulb flat panel displays, and so on.

FIG. 17 shows the optical elements $5^{XXVI}$ arranged in a radial pattern from the outside edges of the film $2^{XII}$ toward the center to redistribute the light ray output distribution of a backlight BL that receives light from cold cathode fluorescent lamp $26^I$ along all four side edges of the backlight.

Figure 18:
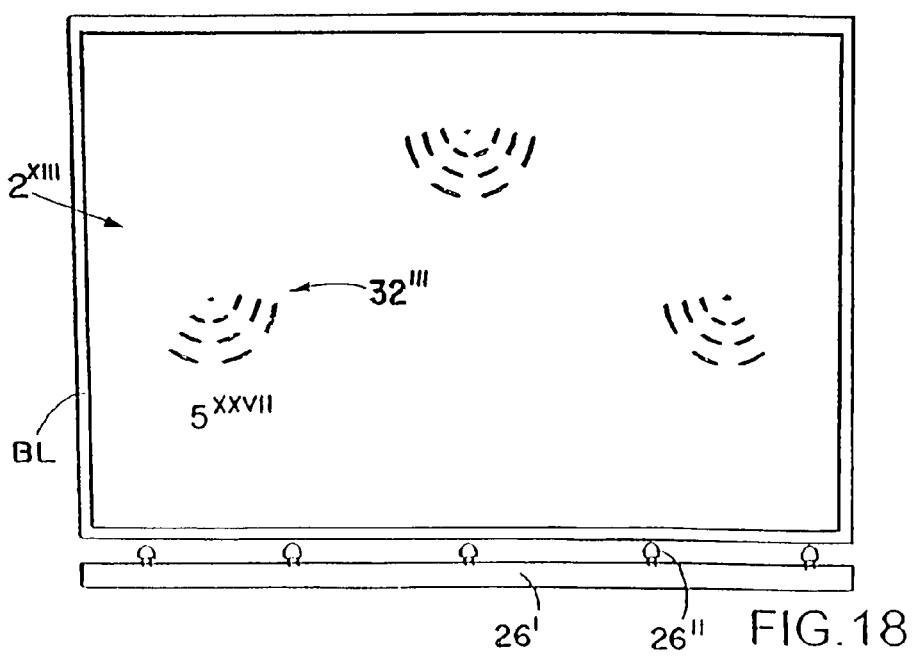

FIG. 18 shows the optical elements $5^{XXVII}$ arranged in a pattern of angled groupings $32^{III}$ across the film 2 that are tailored to redistribute the light ray output distribution of a backlight BL that receives light from one cold cathode fluorescent lamp $26^I$ or a plurality of light emitting diodes $26^{II}$ along one input edge of the backlight.

Figure 19:
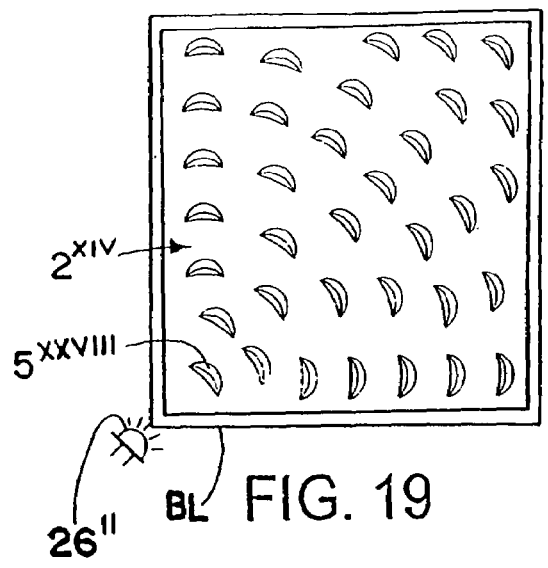
Figure 20:
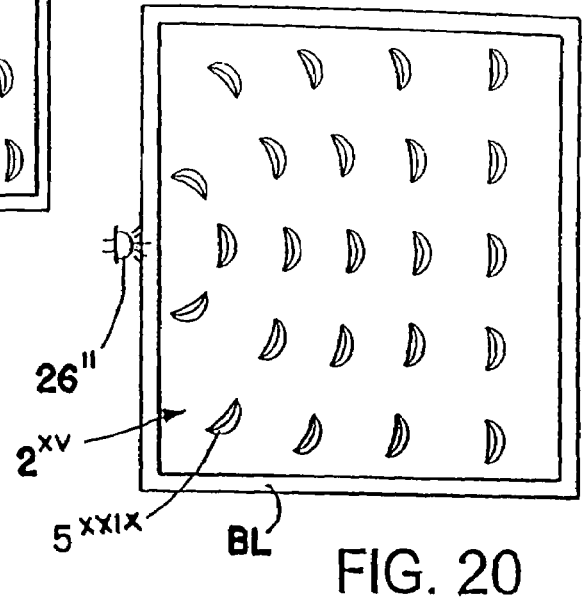

FIG. 19 shows the optical elements $5^{XXVIII}$ arranged in a radial type pattern facing a corner of the film $2^{XIV}$ to redistribute the light ray output distribution of a backlight BL that is corner lit by a light emitting diode $26^{II}$. FIG. 20 shows the optical elements $5^{XXIX}$ arranged in a radial type pattern facing a midpoint on one input edge of the film $2^{XV}$ to redistribute the light ray output distribution of a backlight BL that is lighted at a midpoint of one input edge of the backlight by a single light emitting diode $26^{II}$.

Figure 21:
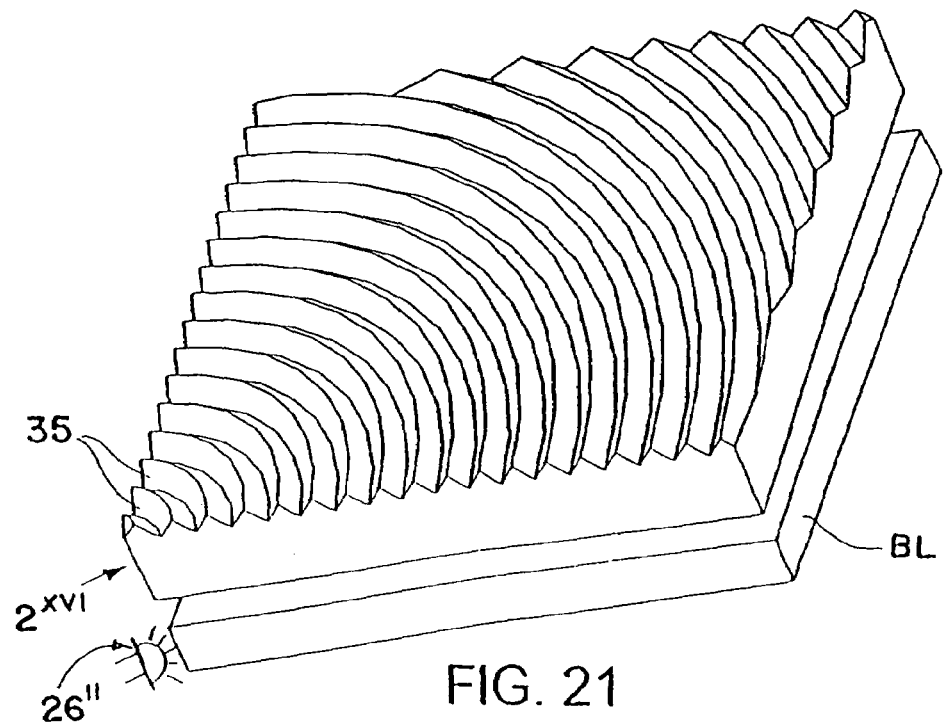
FIG. 21 is a schematic perspective view of a light redirecting film having optical grooves extending across the film in a curved pattern facing a corner of the film.

FIG. 21 shows a light redirecting film $2^{XVI}$ having optical grooves 35 extending across the film in a curved pattern facing a corner of the film to redistribute the light ray output distribution of a backlight BL that is corner lit by a light emitting diode $26^{II}$, whereas FIGS. 22-24 show a light redirecting film $2^{XVII}$ having a pattern of optical grooves $35^I$ extending across the film facing a midpoint along one edge of the film that decreases in curvature as the distance from the one edge increases to redistribute the light ray output distribution of a backlight BL that is edge lit by a light emitting diode $26^{II}$ at a midpoint of one input edge of the backlight.

Where the light redirecting film has a pattern 40 of optical elements 5 thereon that varies along the length of the film, a roll 41 of the film may be provided having a repeating pattern of optical elements thereon as schematically shown in FIG. 15 to permit a selected area of the pattern that best suits a particular application to be die cut from the roll of film.

The backlight BL may be substantially flat, or curved, or may be a single layer or multi-layers, and may have different thicknesses and shapes as desired. Moreover, the backlight may be flexible or rigid, and be made of a variety of compounds. Further, the backlight may be hollow, filled with liquid, air, or be solid, and may have holes or ridges.

Also, the light source 26 may be of any suitable type including, for example, an arc lamp, an incandescent bulb which may also be colored, filtered or painted, a lens end bulb, a line light, a halogen lamp, a light emitting diode (LED), a chip from an LED, a neon bulb, a cold cathode fluorescent lamp, a fiber optic light pipe transmitting from a remote source, a laser or laser diode, or any other suitable light source. Additionally, the light source 26 may be a multiple colored LED, or a combination of multiple colored radiation sources in order to provide a desired colored or white light output distribution. For example, a plurality of colored lights such as LEDs of different colors (e.g., red, blue, green) or a single LED with multiple color chips may be employed to create white light or any other colored light output distribution by varying the intensities of each individual colored light.

A pattern of optical deformities may be provided on one or both sides of the backlight BL or on one or more selected areas on one or both sides of the backlight as desired. As used herein, the term optical deformities means any change in the shape or geometry of a surface and/or coating or surface treatment that causes a portion of the light to be emitted from the backlight. These deformities can be produced in a variety of manners, for example, by providing a painted pattern, an etched pattern, machined pattern, a printed pattern, a hot stamp pattern, or a molded pattern or the like on selected areas of the backlight. An ink or print pattern may be applied for example by pad printing, silk printing, inkjet, heat transfer film process or the like. The deformities may also be printed on a sheet or film which is used to apply the deformities to the backlight. This sheet or film may become a permanent part of the backlight for example by attaching or otherwise positioning the sheet or film against one or both sides of the backlight in order to produce a desired effect.

By varying the density, opaqueness or translucence, shape, depth, color, area, index of refraction or type of deformities on or in an area or areas of the backlight, the light output of the backlight can be controlled. The deformities may be used to control the percent of light output from a light emitting area of the backlight. For example, less and/or smaller size deformities may be placed on surface areas where less light output is wanted. Conversely, a greater percentage of and/or larger deformities may be placed on surface areas of the backlight where greater light output is desired.

Varying the percentages and/or size of deformities in different areas of the backlight is necessary in order to provide a substantially uniform light output distribution. For example, the amount of light traveling through the backlight will ordinarily be greater in areas closer to the light source than in other areas further removed from the light source. A pattern of deformities may be used to adjust for the light variances within the backlight, for example, by providing a denser concentration of deformities with increased distance from the light source thereby resulting in a more uniform light output distribution from the backlight.

The deformities may also be used to control the output ray angle distribution from the backlight to suit a particular application. For example, if the backlight is used to backlight a liquid crystal display, the light output will be more efficient if the deformities (or a light redirecting film is used in combination with the backlight) direct the light rays emitted by the backlight at predetermined ray angles such that they will pass through the liquid crystal display with low loss. Additionally, the pattern of optical deformities may be used to adjust for light output variances attributed to light extractions of the backlight. The pattern of optical deformities may be printed on the backlight surface areas utilizing a wide spectrum of paints, inks, coatings, epoxies or the like, ranging from glossy to opaque or both, and may employ half-tone separation techniques to vary the deformity coverage. Moreover, the pattern of optical deformities may be multiple layers or vary in index of refraction.

Print patterns of optical deformities may vary in shapes such as dots, squares, diamonds, ellipses, stars, random shapes, and the like. Also, print patterns of sixty lines per inch or finer are desirably employed. This makes the deformities or shapes in the print patterns nearly invisible to the human eye in a particular application, thereby eliminating the detection of gradient or banding lines that are common to light extracting patterns utilizing larger elements. Additionally, the deformities may vary in shape and/or size along the length and/or width of the backlight. Also, a random placement pattern of the deformities may be utilized throughout the length and/or width of the backlight. The deformities may have shapes or a pattern with no specific angles to reduce moiré or other interference effects. Examples of methods to create these random patterns are printing a pattern of shapes using stochastic print pattern techniques, frequency modulated half tone patterns, or random dot half tones. Moreover, the deformities may be colored in order to effect color correction in the backlight. The color of the deformities may also vary throughout the backlight, for example, to provide different colors for the same or different light output areas.

In addition to or in lieu of the patterns of optical deformities, other optical deformities including prismatic or lenticular grooves or cross grooves, or depressions or raised surfaces of various shapes using more complex shapes in a mold pattern may be molded, etched, stamped, thermoformed, hot stamped or the like into or on one or more surface areas of the backlight. The prismatic or lenticular surfaces, depressions or raised surfaces will cause a portion of the light rays contacted thereby to be emitted from the backlight. Also, the angles of the prisms, depressions or other surfaces may be varied to direct the light in different directions to produce a desired light output distribution or effect. Moreover, the reflective or refractive surfaces may have shapes or a pattern with no specific angles to reduce moiré or other interference effects.

A back reflector 42 may be attached or positioned against one side of the backlight BL as schematically shown in FIGS. 1 and 2 in order to improve light output efficiency of the backlight by reflecting the light emitted from that side back through the backlight for emission through the opposite side. Additionally, a pattern of optical deformities 50 may be provided on one or both sides of the backlight as schematically shown in FIGS. 1 and 2 in order to change the path of the light so that the internal critical angle is exceeded and a portion of the light is emitted from one or both sides of the backlight.

FIGS. 25-28 show optical deformities $50^I$, $50^{II}$ which may either be individual projections 51 on the respective backlight surface areas 52 or individual depressions 53 in such surface areas $52^I$ of a backlight $BL^I$, $BL^{II}$. In either case, each of these optical deformities has a well defined shape including a reflective or refractive surface 54, $54^I$ (hereafter sometimes collectively referred to as a reflective/refractive surface) that intersects the respective backlight surface area 52, $52^I$ at one edge 55, $55^I$ and has a uniform slope throughout its length for more precisely controlling the emission of light by each of the deformities. Along a peripheral edge portion 56, $56^I$ of each reflective/refractive surface 54, $54^I$ is an end wall 57, $57^I$ of each deformity that intersects the respective panel surface area 52, $52^I$ at a greater included angle I, $I^I$ than the included angle $I^{II}$, $I^{III}$ between the reflective/refractive surfaces 54, $54^I$ and the panel surface area 52, $52^I$ (see FIGS. 27 and 28) to minimize the projected surface area of the end walls on the panel surface area. This allows more deformities to be placed on or in the panel surface areas than would otherwise be possible if the projected surface areas of the end walls 57, $57^I$ were substantially the same as or greater than the projected surface areas of the reflective/refractive surfaces 54, $54^I$.

Figure 25:
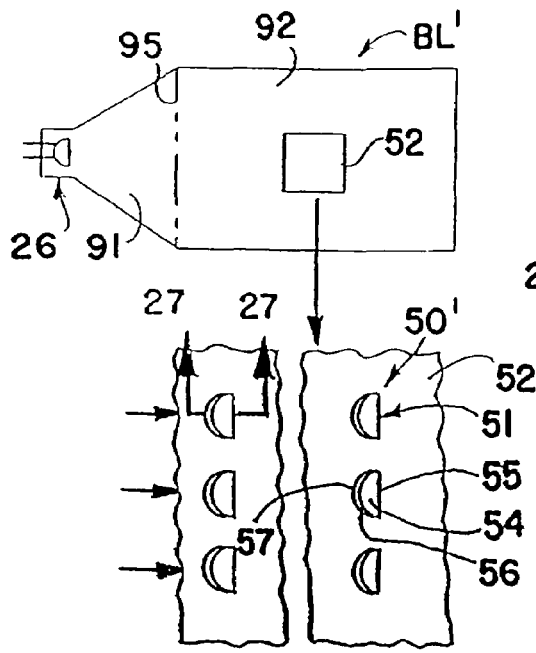
FIGS. 25 and 26 are enlarged schematic fragmentary plan views of a surface area of a backlight/light emitting panel assembly showing various forms of optical deformities formed on or in a surface of the backlight.
Figure 26:
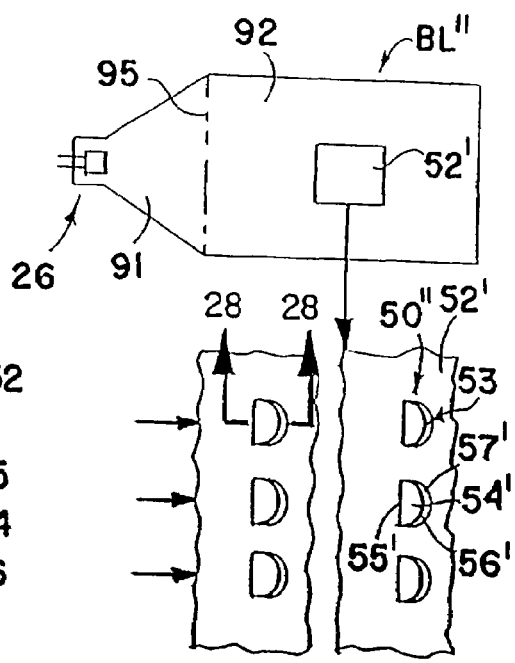
Figure 28:
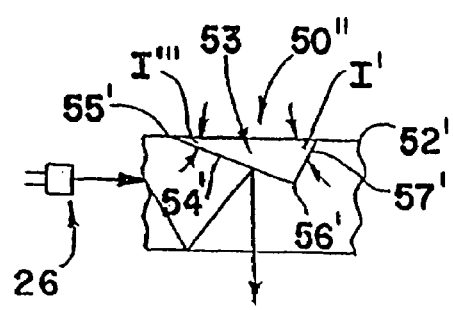
Figure 29:
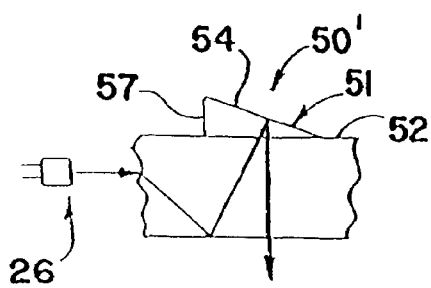
FIGS. 29 and 30 are enlarged schematic longitudinal sections through other forms of optical deformities formed on or in a surface of a backlight.
Figure 30:
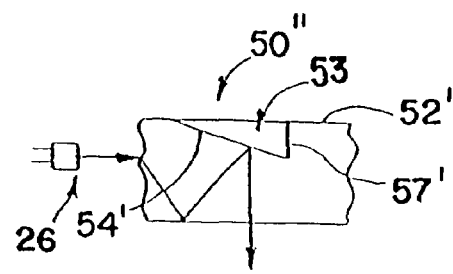

In FIGS. 25 and 26 the peripheral edge portions 56, $56^I$ of the reflective/refractive surfaces 54, $54^I$ and associated end walls 57, $57^I$ are curved in the transverse direction. Also in FIGS. 27 and 28 the end walls 57, $57^I$ of the deformities are shown extending substantially perpendicular to the reflective/refractive surfaces 54, $54^I$ of the deformities. Alternatively, such end walls may extend substantially perpendicular to the panel surface areas 52, $52^I$ as schematically shown in FIGS. 29 and 30. This virtually eliminates any projected surface area of the end walls on the panel surface areas whereby the density of the deformities on the panel surface areas may be even further increased.

Figure 31:
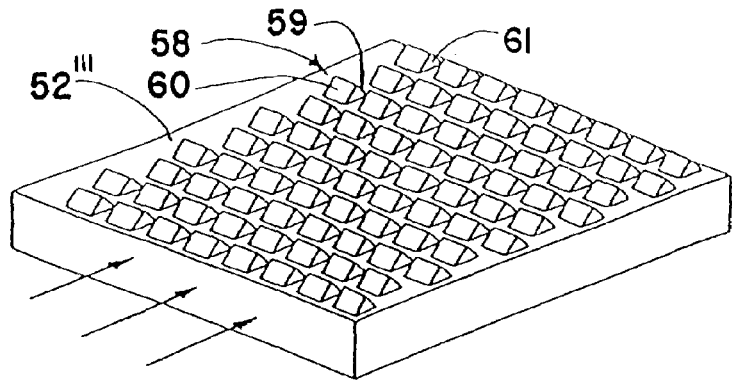
FIGS. 31-39 are enlarged schematic perspective views of backlight surface areas containing various patterns of individual optical deformities of other well defined shapes.
Figure 32:
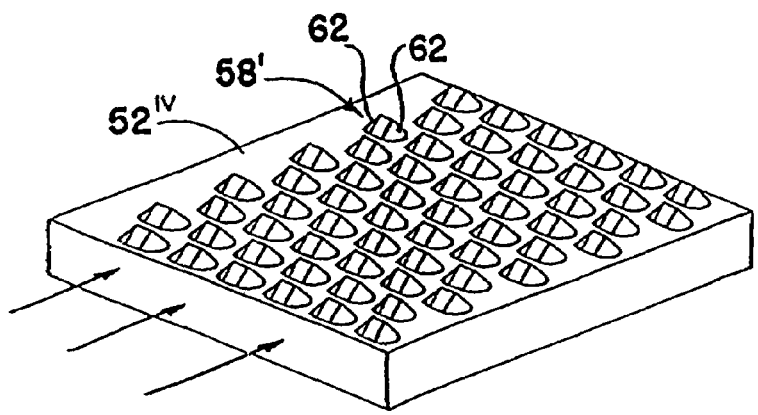

The optical deformities may also be of other well defined shapes to obtain a desired light output distribution from a panel surface area. FIG. 31 shows individual light extracting deformities 58 on a panel surface area $52^{III}$ each including a generally planar, rectangular reflective/refractive surface 59 and associated end wall 60 of a uniform slope throughout their length and width and generally planar side walls 61. Alternatively, the deformities 58' may have rounded or curved side walls 62 on a panel surface area $52^{IV}$ as schematically shown in FIG. 32.

Figure 33:
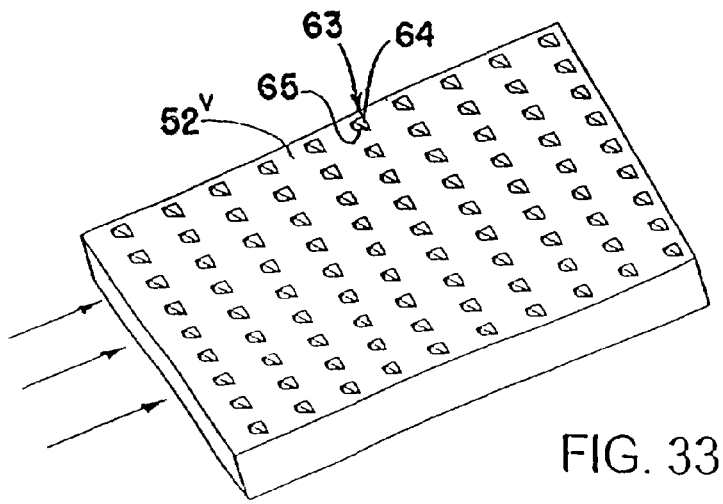
Figure 34:
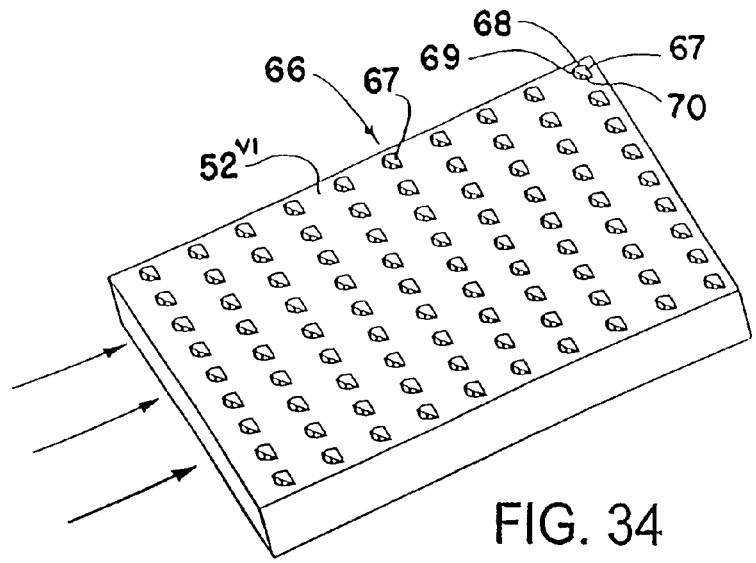

FIG. 33 shows individual light extracting deformities 63 on a panel surface area $52^V$ each including a planar, sloping triangular shaped reflective/refractive surface 64 and associated planar, generally triangularly shaped side walls or end walls 65. FIG. 34 shows individual light extracting deformities 66 on a panel surface area $52^{VI}$ each including a planar sloping reflective/refractive surface 67 having angled peripheral edge portions 68 and associated angled end and side walls 69 and 70.

Figure 35:
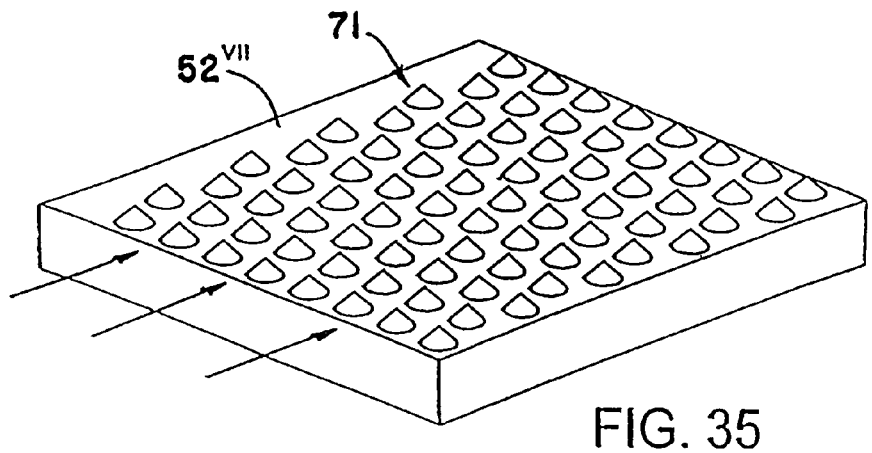
Figure 36:
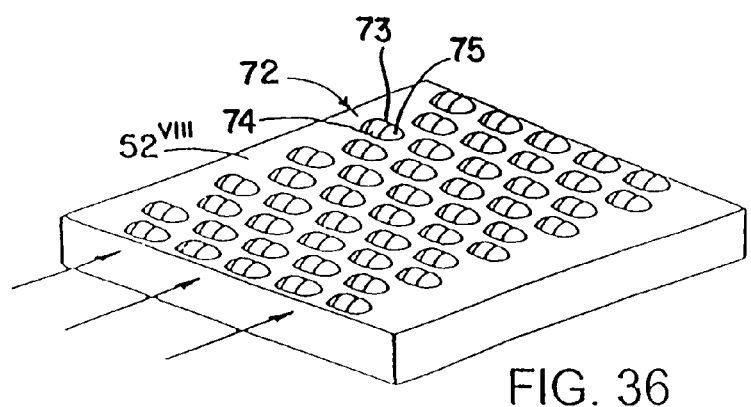

FIG. 35 shows individual light extracting deformities 71 on a panel surface area $52^{VII}$ which are generally conically shaped, whereas FIG. 36 shows individual light extracting deformities 72 on a panel surface area $52^{VIII}$ each including a rounded reflective/refractive surface 73 and rounded end walls 74 and rounded or curved side walls 75 all blended together. These additional surfaces will reflect or refract other light rays impinging thereon in different directions to spread light across the backlight/panel member BL to provide a more uniform distribution of light emitted from the panel member.

Figure 27:
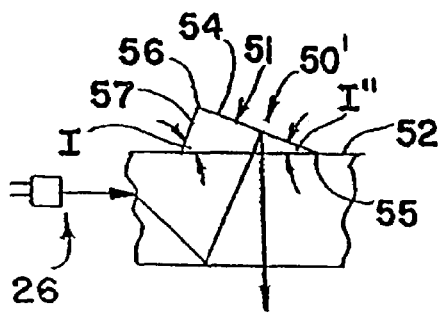
FIGS. 27 and 28 are enlarged longitudinal sections through one of the optical deformities of FIGS. 25 and 26, respectively.
Figure 37:
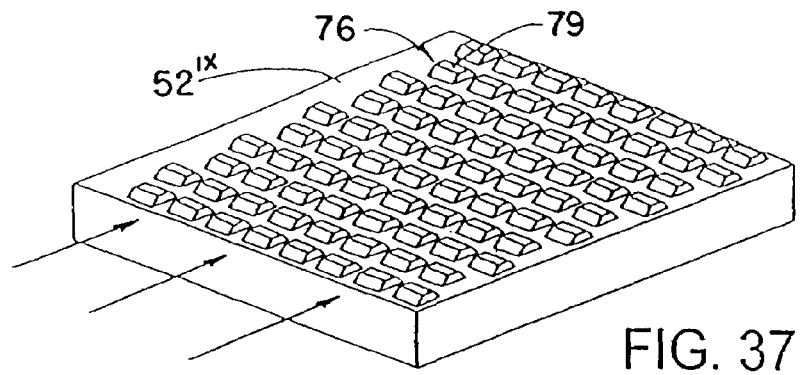
Figure 38:
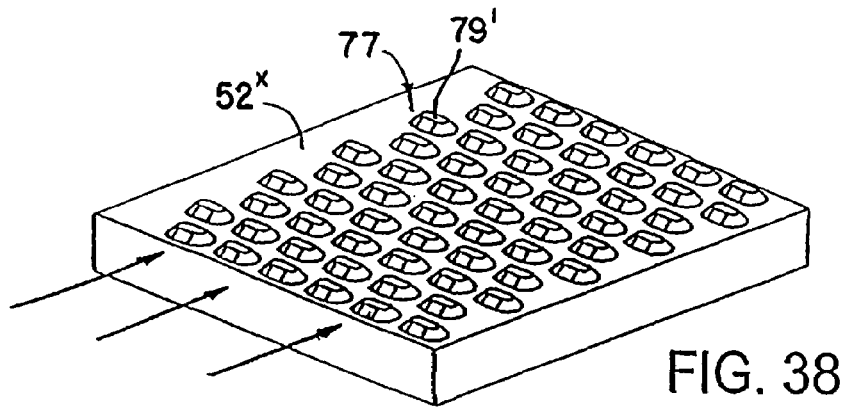
Figure 39:
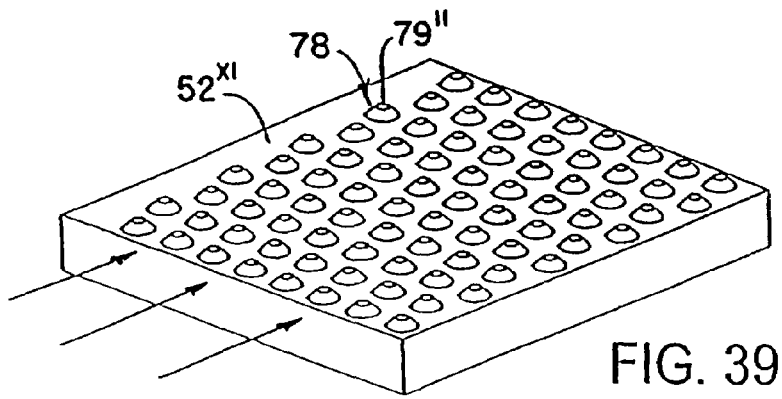
Figure 40:
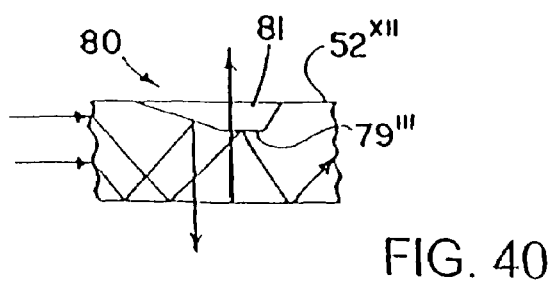
FIG. 40 is an enlarged schematic longitudinal section through another form of optical deformity formed on or in a surface of a backlight.

Regardless of the particular shape of the reflective/refractive surfaces and end and side walls of the individual deformities, such deformities may also include planar surfaces intersecting the reflective/refractive surfaces and end and/or side walls in parallel spaced relation to the panel surface areas 52. FIGS. 37-39 show deformities 76, 77 and 78 in the form of individual projections on a panel surface area $52^{IX}$, $52^X$, $52^{XI}$ having representative shapes similar to those shown in FIGS. 31, 32 and 35, respectively, except that each deformity is intersected by a planar surface 79, $79^I$, $79^{II}$ in parallel spaced relation to the panel surface area. In like manner, FIG. 40 shows one of a multitude of deformities 80 in the form of individual depressions 81 in a panel surface area $52^{XII}$ each intersected by a planar surface $79^{III}$ in parallel spaced relation to the general planar surface of the panel surface area. Any light rays that impinge on such planar surfaces at internal angles less than the critical angle for emission of light from the panel surface area will be internally reflected by the planar surfaces, whereas any light rays impinging on such planar surfaces at internal angles greater than the critical angle will be emitted by the planar surfaces with minimal optical discontinuities, as schematically shown in FIG. 40.

Where the deformities are projections on the panel surface area, the reflective/refractive surfaces extend at an angle away from the panel in a direction generally opposite to that in which the light rays from the light source 26 travel through the panel as schematically shown in FIGS. 27 and 29. Where the deformities are depressions in the panel surface area, the reflective/refractive surfaces extend at an angle into the panel in the same general direction in which the light rays from the light source 26 travel through the panel member as schematically shown in FIGS. 28 and 30.

Figure 41:
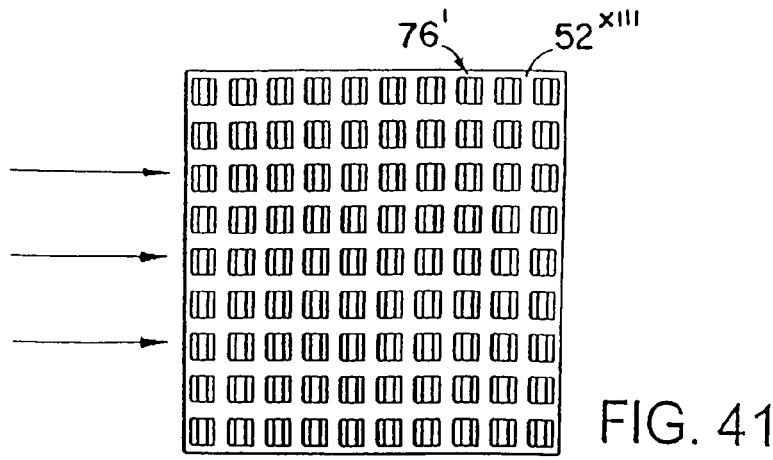
FIGS. 41 and 42 are enlarged schematic top plan views of backlight surface areas containing optical deformities similar in shape to those shown in FIGS. 37 and 38 arranged in a plurality of straight rows along the length and width of the surface areas.
Figure 42:
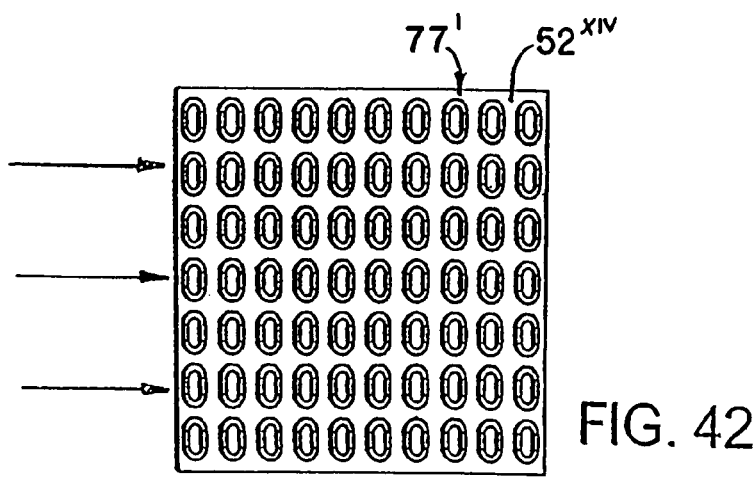
Figure 43:
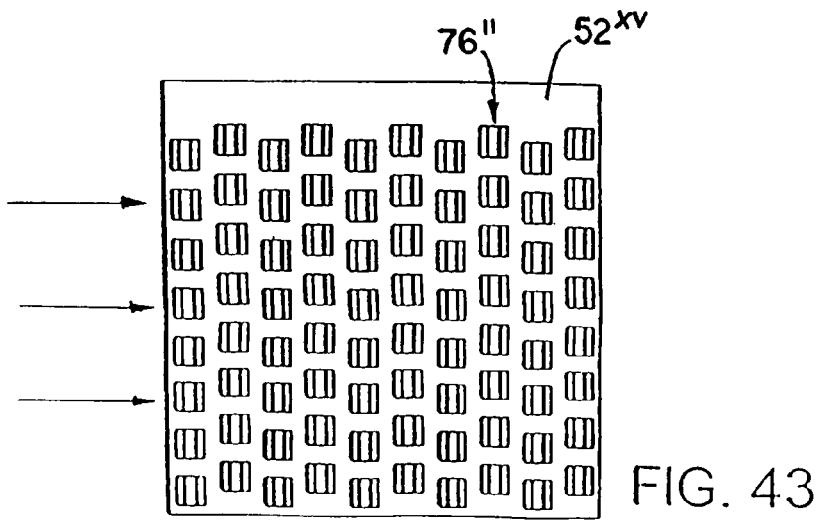
FIGS. 43 and 44 are enlarged schematic top plan views of backlight surface areas containing optical deformities also similar in shape to those shown in FIGS. 37 and 38 arranged in staggered rows along the length of the surface areas.
Figure 44:
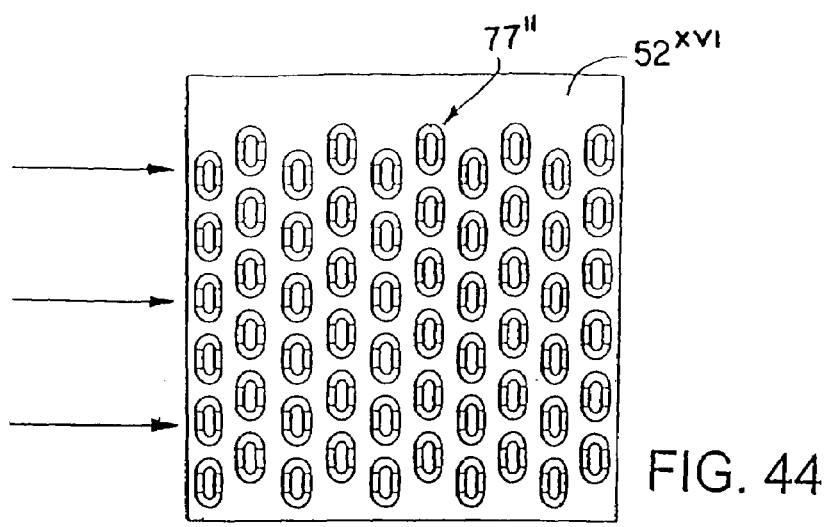

Regardless of whether the deformities are projections or depressions on or in the panel surface areas, the slopes of the light reflective/refractive surfaces of the deformities may be varied to cause the light rays impinging thereon to be either refracted out of the light emitting panel or reflected back through the panel and emitted out the opposite side of the panel which may be etched to diffuse the light emitted therefrom or covered by a light redirecting film to produce a desired effect. Also, the pattern of optical deformities on the panel surface area may be uniform or variable as desired to obtain a desired light output distribution from the panel surface areas. FIGS. 41 and 42 show deformities $76^I$ and $77^I$ similar in shape to those shown in FIGS. 37 and 38 arranged in a plurality of generally straight uniformly spaced apart rows along the length and width of a panel surface area $52^{XIII}$, $52^{XIV}$, whereas FIGS. 43 and 44 show such deformities $76^{II}$ and $77^{II}$ arranged in staggered rows that overlap each other along the length of a panel surface area $52^{XV}$, $52^{XVI}$.

Figure 45:
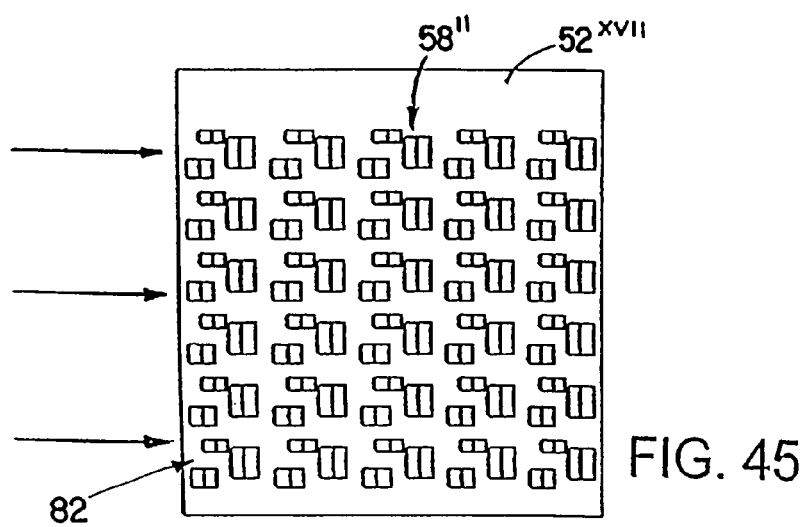
FIGS. 45 and 46 are enlarged schematic top plan views of backlight surface areas containing a random or variable pattern of different sized optical deformities on the surface areas.
Figure 46:
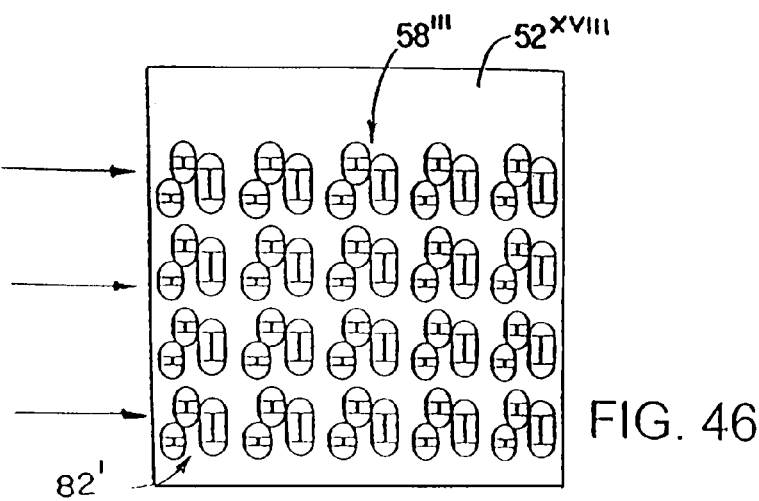
Figure 47:
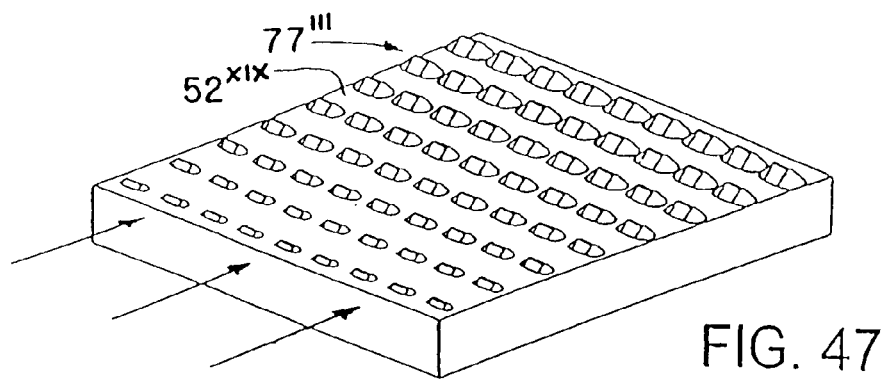
FIG. 47 is an enlarged schematic perspective view of a backlight surface area showing optical deformities increasing in size as the distance of the deformities from the light input surface increases or intensity of the light increases along the length of the surface area.

Also, the size, including the width, length and depth or height as well as the angular orientation and position of the optical deformities may vary along the length and/or width of any given panel surface area to obtain a desired light output distribution from the panel surface area. FIGS. 45 and 46 show a random or variable pattern of different size deformities $58^{II}$, $58^{III}$ similar in shape to those shown in FIGS. 31 and 32, respectively, arranged in staggered rows on a panel surface area $52^{XVII}$, $52^{XVIII}$, whereas FIG. 47 shows deformities $77^{III}$ similar in shape to those shown in FIG. 38 increasing in size as the distance of the deformities from the light source increases or intensity of the light decreases along the length and/or width of the panel surface area $52^{XIX}$. The deformities are shown in FIGS. 45 and 46 arranged in clusters 82, $82^{I}$ across the panel surface, with at least some of the deformities in each cluster having a different size or shape characteristic that collectively produce an average size or shape characteristic for each of the clusters that varies across the panel surface. For example, at least some of the deformities in each of the clusters may have a different depth or height or different slope or orientation that collectively produce an average depth or height characteristic or average slope or orientation of the sloping surface that varies across the panel surface. Likewise at least some of the deformities in each of the clusters may have a different width or length that collectively produce an average width or length characteristic that varies across the panel surface. This allows one to obtain a desired size or shape characteristic beyond machinery tolerances, and also defeats moiré and interference effects.

Figure 48:
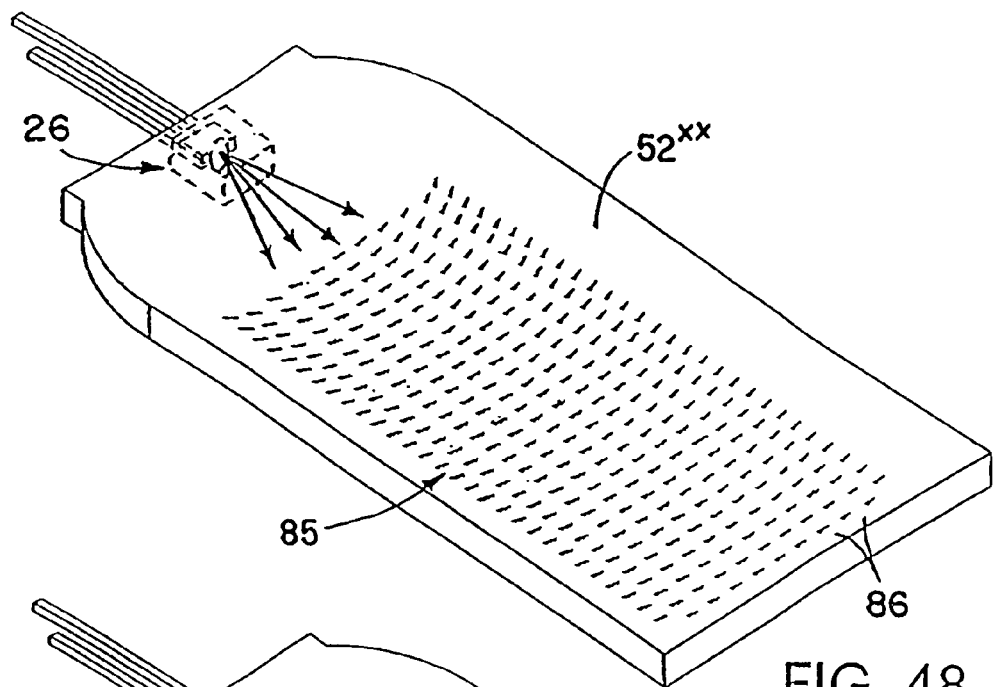
FIGS. 48 and 49 are schematic perspective views showing different angular orientations of the optical deformities along the length and width of a backlight surface area.
Figure 49:
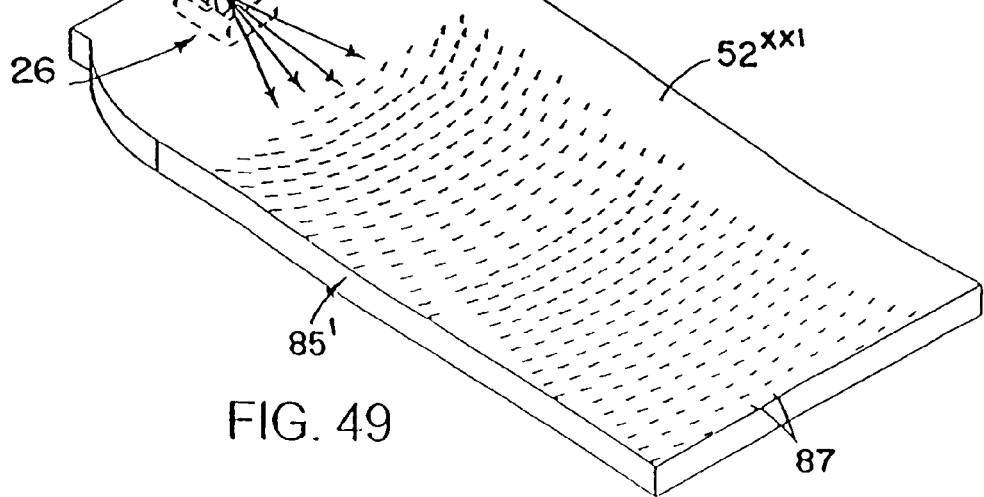

FIGS. 48 and 49 schematically show different angular orientations of optical deformities 85, $85^{I}$ of any desired shape along the length and width of a panel surface area, $52^{XX}$, $52^{XXI}$ of a light emitting panel assembly backlight. In FIG. 48 the deformities are arranged in straight rows 86 along the length of the panel surface area but the deformities in each of the rows are oriented to face the light source 26 so that all of the deformities are substantially in line with the light rays being emitted from the light source. In FIG. 49 the deformities $85^{I}$ are also oriented to face the light source 26 similar to FIG. 48. In addition, the rows 87 of deformities in FIG. 49 are in substantial radial alignment with the light source 26.

FIGS. 50 and 51 schematically show how exemplary light rays 90, $90^{I}$ emitted from a focused light source 26 insert molded or cast within a light transition area 91, $91^{I}$ of a light emitting panel assembly backlight $BL^{III}$, $BL^{IV}$ in accordance with this invention are reflected during their travel through the light emitting panel member 92, $92^{I}$ until they impinge upon individual light extracting deformities $50^{III}$, $77^{IV}$ of well defined shapes on or in a panel surface area $52^{XXII}$, $52^{XXIII}$ causing more of the light rays to be reflected or refracted out of one side 93, $93^{I}$ of the panel member than the other side 94, $94^{I}$. In FIG. 50 the exemplary light rays 90 are shown being reflected by the reflective/refractive surfaces $54^{III}$ of the deformities $50^{III}$ in the same general direction out through the same side 93 of the panel member, whereas in FIG. 51 the light rays $90^{I}$ are shown being scattered in different directions within the panel member $92^{I}$ by the rounded side walls $62^{I}$ of the deformities $77^{IV}$ before the light rays are reflected/refracted out of the same side $93^{I}$ of the panel member. Such a pattern of individual light extracting deformities of well defined shapes in accordance with the present invention can cause 60 to 70% or more of the light received through the input edge $95^{I}$ of the panel member to be emitted from the same side of the panel member.

From the foregoing, it will be apparent that the light redirecting films of the present invention redistribute more of the light emitted by a backlight or other light source toward a direction more normal to the plane of the films. Also, the light redirecting films and backlights of the present invention may be tailored or tuned to each other to provide a system in which the individual optical elements of the light redirecting films work in conjunction with the optical deformities of the backlights to produce an optimized output light ray angle distribution from the system.

Although the invention has been shown and described with respect to certain embodiments, it is obvious that equivalent alterations and modifications will occur to others skilled in the art upon the reading and understanding of the specification. In particular, with regard to the various functions performed by the above described components, the terms (including any reference to a "means") used to describe such components are intended to correspond, unless otherwise indicated, to any component which performs the specified function of the described component (e.g., that is functionally equivalent), even though not structurally equivalent to the disclosed component which performs the function in the herein illustrated exemplary embodiments of the invention. In addition, while a particular feature of the invention may have been disclosed with respect to only one embodiment, such feature may be combined with one or more other features of other embodiments as may be desired and advantageous for any given or particular application.

What is claimed is:

1. A light redirecting film comprising a thin optically transparent substrate having a pattern of individual optical elements of well defined shape on or in the substrate, the optical elements being quite small in relation to a width and length of the substrate, at least some of the optical elements varying at different locations on the substrate to redistribute light passing through the substrate toward a direction normal to the substrate, wherein the substrate has multiple layers and at least some of the multiple layers have different indices of refraction.

2. The film of claim 1 wherein at least some of the optical elements vary in at least one of the following characteristics: slope angle, density, position, orientation, height or depth, shape, and size, to tailor the film to the light output distribution of different backlights.

3. The film of claim 1 wherein at least some of the optical elements have a different beam profile at different locations on the substrate.

4. The film of claim 1 wherein the size and shape of the optical elements are tailored to redistribute more of the light emitted by a light source within a desired viewing angle.

5. The film of claim 1 wherein at least some of the optical elements overlap, intersect, or interlock each other.

6. The film of claim 1 wherein at least some of the optical elements are oriented at different angles across the substrate for redirecting the light along different axes.

7. The film of claim 1 wherein the size of at least some of the optical elements varies across the substrate.

8. The film of claim 1 wherein the shape of at least some of the optical elements varies across the substrate.

9. The film of claim 1 wherein the height or depth of at least some of the optical elements varies across the substrate.

10. The film of claim 1 wherein the position of at least some of the optical elements varies across the substrate.

11. The film of claim 1 wherein the density of the optical elements varies across the substrate.

12. The film of claim 1 wherein at least some of the optical elements vary in a predetermined pattern to redistribute light within a desired optical distribution.

13. The film of claim 1 wherein at least some of the optical elements have at least one curved surface and at least one planar surface.

14. The film of claim 1 wherein at least some of the optical elements are randomly distributed across the substrate.

15. The film of claim 1 wherein at least some of the optical elements have an angled surface that varies in area across the substrate.

16. The film of claim 1 wherein the individual optical elements are on opposite sides of the substrate.

17. The film of claim 1 wherein at least some of the optical elements include a combination of planar and curved surfaces, the ratio of the areas of the planar and curved surfaces being selected to produce a desired viewing angle.

18. The film of claim 1 in combination with a backlight including a panel surface having a light ray output distribution that varies at different locations on the panel surface, wherein the light redirecting film is in close proximity to the panel surface, and wherein the backlight includes perimeter lighting, and the optical elements are arranged in a pattern that is tailored to redistribute the light ray output distribution of the backlight that receives light from the perimeter lighting.

19. The film of claim 1 in combination with a backlight including a panel surface having a light ray output distribution that varies at different locations on the panel surface, wherein the light redirecting film is in close proximity to the panel surface, and wherein the backlight includes at least one corner light, and the optical elements are arranged in a radial type pattern that is tailored to redistribute the light ray output distribution of the backlight that receives light from the corner light.

20. The film of claim 1 in combination with a light source, wherein one side of the light redirecting film substrate is in close proximity to the light source with an air gap therebetween, and wherein at least some light that is emitted by the light source passes through the one side of the substrate and out an opposite side of the substrate to redistribute the light toward a direction normal to the substrate.

21. The film of claim 1 wherein the substrate has a coating to produce a specific effect.

22. The film of claim 21 wherein the coating is selective.

23. The film of claim 1 wherein at least some of the optical elements have at least two different shaped surface parameters.

24. The film of claim 23 wherein one of the different shaped surfaces is curved, and the other of the different shaped surfaces is planar.

25. The film of claim 1 wherein at least some of the optical elements have only two surfaces, both of which intersect each other to form a ridge and both of which intersect the substrate or another optical element.

26. The film of claim 25 wherein the ridges of at least some of the optical elements have ends that intersect the substrate or other optical elements where the ridges end.

27. The film of claim 1 in combination with a backlight including a panel surface having a light ray output distribution that varies at different locations on the panel surface, wherein the light redirecting film is in close proximity to the panel surface, and wherein the backlight includes at least one cold cathode fluorescent light source and at least one input edge that receives light from the light source, and the optical elements are arranged in a pattern that is tailored to redistribute the light ray output distribution of the backlight that receives light from the cold cathode fluorescent light source toward a direction normal to the substrate.

28. The film and backlight of claim 27 wherein the backlight includes two or more cold cathode fluorescent light sources and two or more input edges that receive light from the light sources, and the optical elements are arranged in a pattern that is tailored to redistribute the light ray output distribution of the backlight that receives light from the two or more cold cathode fluorescent light sources toward a direction normal to the substrate.

29. The film of claim 1 in combination with a backlight including a panel surface having a light ray output distribution that varies at different locations on the panel surface, wherein the light redirecting film is in close proximity to the panel surface, and wherein the backlight includes a single focused light source, and the optical elements are arranged in a radial type pattern that is tailored to redistribute the light ray output distribution of the backlight that is lighted by the single focused light source.

30. The film and backlight of claim 29 wherein the light source is a light emitting diode.

31. The film of claim 1 in combination with a backlight including a panel surface having a light ray output distribution that varies at different locations on the panel surface, wherein the light redirecting film is in close proximity to the panel surface, and wherein the backlight includes a single light emitting diode light source and an input edge that receives light from the light source, and the optical elements are arranged in a pattern that is tailored to redistribute the light ray output distribution of the backlight that receives light from the light source.

32. The film and backlight of claim 31 wherein the backlight includes a plurality of light emitting diode light sources and at least one input edge that receives light from the light sources, and the optical elements are arranged in a pattern that is tailored to redistribute the light ray output distribution of the backlight that receives light from the plurality of light sources.

33. The film and backlight of claim 32 wherein the light emitting diode light sources are different colored light sources that produce different colors of light that are mixed to provide a substantially white light output distribution.

34. The film and backlight of claim 32 wherein the backlight includes two or more input edges that receive light from two or more of the light emitting diode light sources.

35. A light redirecting film comprising a thin optically transparent substrate having a pattern of individual optical elements of well defined shape on or in the substrate, the optical elements being quite small in relation to a width and length of the substrate, at least some of the optical elements varying at different locations on the substrate to redistribute light passing through the substrate toward a direction normal to the substrate, wherein at least some of the optical elements have a pair of oppositely angled sides and a pair of oppositely curved ends.

36. The film of claim 35 wherein the oppositely angled sides intersect each other.

37. The film of claim 35 wherein at least some of the optical elements have a curved top surface intersecting the oppositely angled sides and oppositely curved ends.

38. The film of claim 35 in combination with a light source, wherein one side of the light redirecting film substrate is in close proximity to the light source with an air gap therebetween, and wherein at least some light that is emitted by the light source passes through the one side of the substrate and out an opposite side of the substrate to redistribute the light toward a direction normal to the substrate.

39. A light redirecting film comprising a thin optically transparent substrate having a pattern of individual optical elements of well defined shape on or in the substrate, the optical elements being quite small in relation to a width and length of the substrate, at least some of the optical elements varying at different locations on the substrate to redistribute light passing through the substrate toward a direction normal to the substrate, wherein the substrate has a coating to produce a specific effect and the coating has a different index of refraction than the substrate.

40. The film of claim 39 in combination with a light source, wherein one side of the light redirecting film substrate is in close proximity to the light source with an air gap therebetween, and wherein at least some light that is emitted by the light source passes through the one side of the substrate and out an opposite side of the substrate to redistribute the light toward a direction normal to the substrate.

41. A light redirecting film comprising a thin optically transparent substrate having a pattern of individual optical elements of well defined shape on or in the substrate, the optical elements being quite small in relation to a width and length of the substrate, at least some of the optical elements varying at different locations on the substrate to redistribute light passing through the substrate toward a direction normal to the substrate, wherein at least some of the optical elements have different slope angles.

42. The film of claim 41 in combination with a light source, wherein one side of the light redirecting film substrate is in close proximity to the light source with an air gap therebetween, and wherein at least some light that is emitted by the light source passes through the one side of the substrate and out an opposite side of the substrate to redistribute the light toward a direction normal to the substrate.

* * * * *